US008597320B2

(12) United States Patent
Sepetka et al.

(10) Patent No.: US 8,597,320 B2
(45) Date of Patent: Dec. 3, 2013

(54) DEVICES AND METHODS FOR TREATING VASCULAR MALFORMATIONS

(75) Inventors: Ivan Sepetka, Los Altos, CA (US); Martin S. Dieck, Cupertino, CA (US); Ryan Pierce, Mountain View, CA (US); Maria Aboytes, East Palo Alto, CA (US); Son Gia, San Jose, CA (US)

(73) Assignee: Concentric, Medical, Inc., Mountain View, CA (US)

( * ) Notice: Subject to any disclaimer, the term of this patent is extended or adjusted under 35 U.S.C. 154(b) by 0 days.

(21) Appl. No.: 13/114,635

(22) Filed: May 24, 2011

(65) Prior Publication Data

US 2011/0224776 A1    Sep. 15, 2011

Related U.S. Application Data

(63) Continuation of application No. 12/653,821, filed on Dec. 21, 2009, which is a continuation of application No. 10/106,870, filed on Mar. 25, 2002, now abandoned, which is a continuation-in-part of application No. 09/695,637, filed on Oct. 24, 2000, now Pat. No. 6,746,468, which is a continuation-in-part of application No. 09/324,359, filed on Jun. 2, 1999, now Pat. No. 6,375,668.

(51) Int. Cl.
*A61M 29/00*    (2006.01)

(52) U.S. Cl.
USPC .......................................................... 606/200

(58) Field of Classification Search
None
See application file for complete search history.

(56) References Cited

U.S. PATENT DOCUMENTS

| | | | |
|---|---|---|---|
| 4,735,201 A | 4/1988 | O'Reilly |
| 5,108,407 A | 4/1992 | Geremia et al. |
| 5,258,042 A | 11/1993 | Mehta |
| 5,360,443 A | 11/1994 | Barone et al. |
| 5,368,566 A | 11/1994 | Crocker |
| 5,415,637 A | 5/1995 | Khosravi |
| 5,676,685 A | 10/1997 | Razavi |
| 5,749,894 A | 5/1998 | Engelson |
| 5,823,198 A | 10/1998 | Jones et al. |
| 5,916,235 A | 6/1999 | Guglielmi |
| 5,928,260 A | 7/1999 | Chin et al. |
| 5,935,148 A | 8/1999 | Villar et al. |

(Continued)

FOREIGN PATENT DOCUMENTS

| | | |
|---|---|---|
| WO | WO 97/26939 | 7/1997 |
| WO | WO 98/10187 | 3/1998 |

(Continued)

OTHER PUBLICATIONS

O'Reilly et al., "Laser-Induced Thermal Occlusion of Berry Aneurysms: Initial Experimental Results," Radiology 1989; 171:471-474.

*Primary Examiner* — Melanie Tyson
(74) *Attorney, Agent, or Firm* — Vista IP Law Group LLP

(57) ABSTRACT

A method of filling an aneurysm is described which includes the step of advancing a device through a patient's vascular system to an aneurysm and positioning the device within the aneurysm. The device has a closed mesh structure forming by a plurality of flexible filaments. The device also has a proximal collar and a distal collar with the flexible filaments extending therebetween. The closed mesh structure is movable from a collapsed configuration to an expanded configuration.

3 Claims, 44 Drawing Sheets

(56) References Cited

U.S. PATENT DOCUMENTS

| | | |
|---|---|---|
| 5,951,599 A | 9/1999 | McCrory |
| 5,980,554 A | 11/1999 | Lenker et al. |
| 6,036,720 A | 3/2000 | Abrams et al. |
| 6,048,333 A | 4/2000 | Lennox et al. |
| 6,152,144 A | 11/2000 | Lesh et al. |
| 6,183,495 B1 | 2/2001 | Lenker et al. |
| 6,193,708 B1 | 2/2001 | Ken et al. |
| 6,635,068 B1 * | 10/2003 | Dubrul et al. ................. 606/200 |

FOREIGN PATENT DOCUMENTS

| | | |
|---|---|---|
| WO | WO 98/23227 | 6/1998 |
| WO | WO 98/50102 | 11/1998 |
| WO | WO 99/02092 | 1/1999 |
| WO | WO 99/02093 | 1/1999 |
| WO | WO 99/03404 | 1/1999 |
| WO | WO 99/05977 | 2/1999 |
| WO | WO 99/07293 | 2/1999 |
| WO | WO 99/07294 | 2/1999 |
| WO | WO 99/08607 | 2/1999 |

* cited by examiner

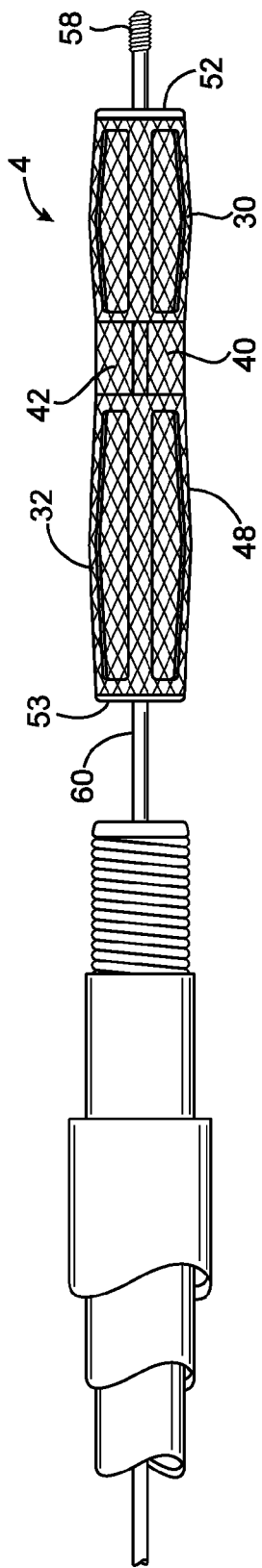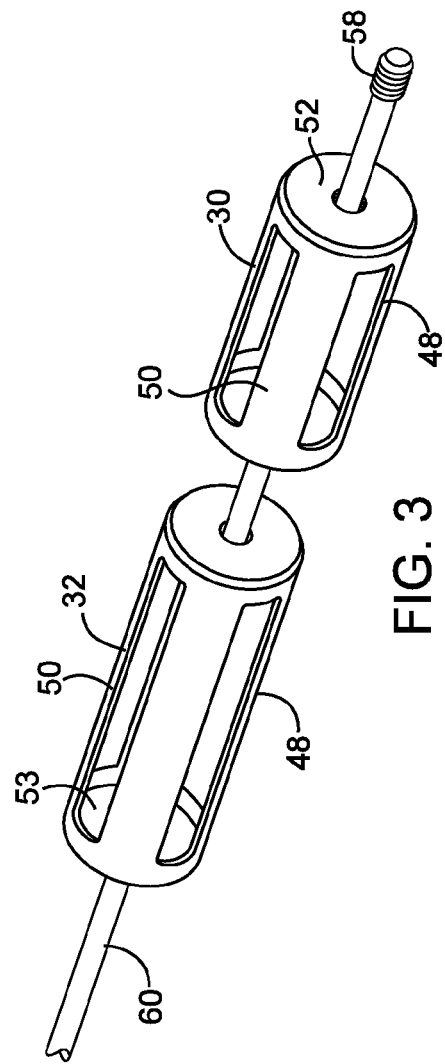

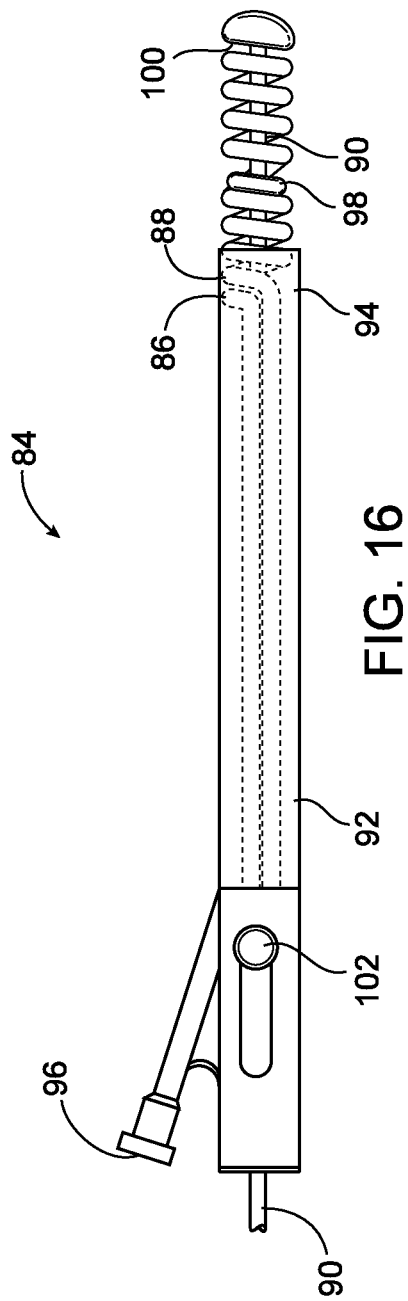
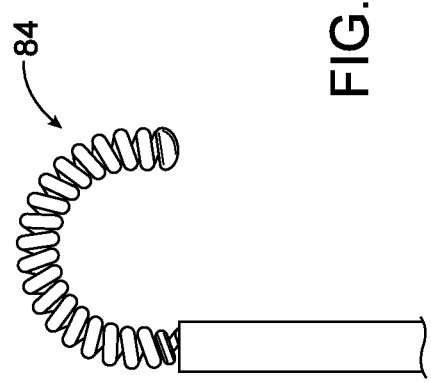
FIG. 16
FIG. 17

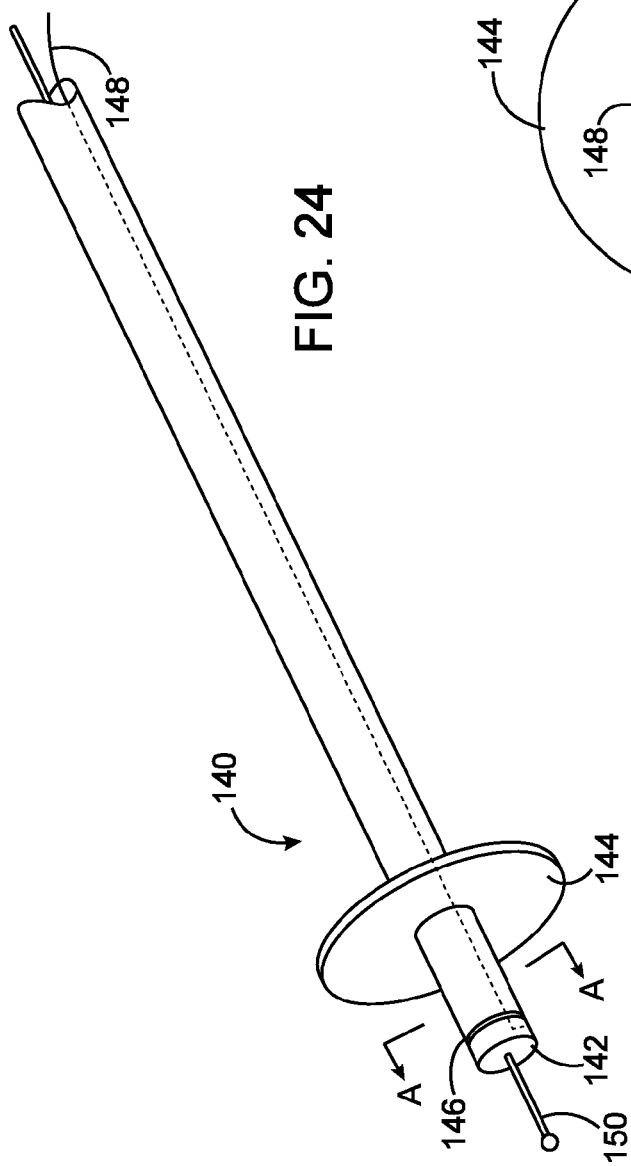
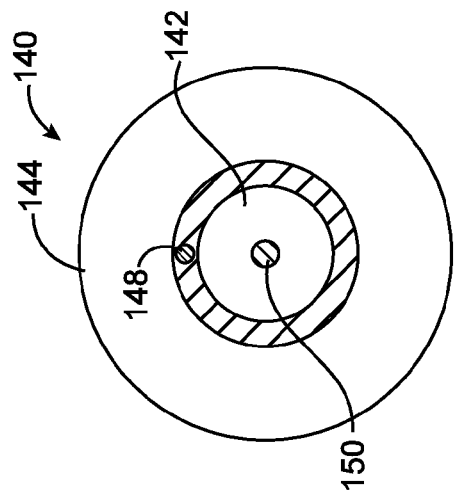
FIG. 24
FIG. 25

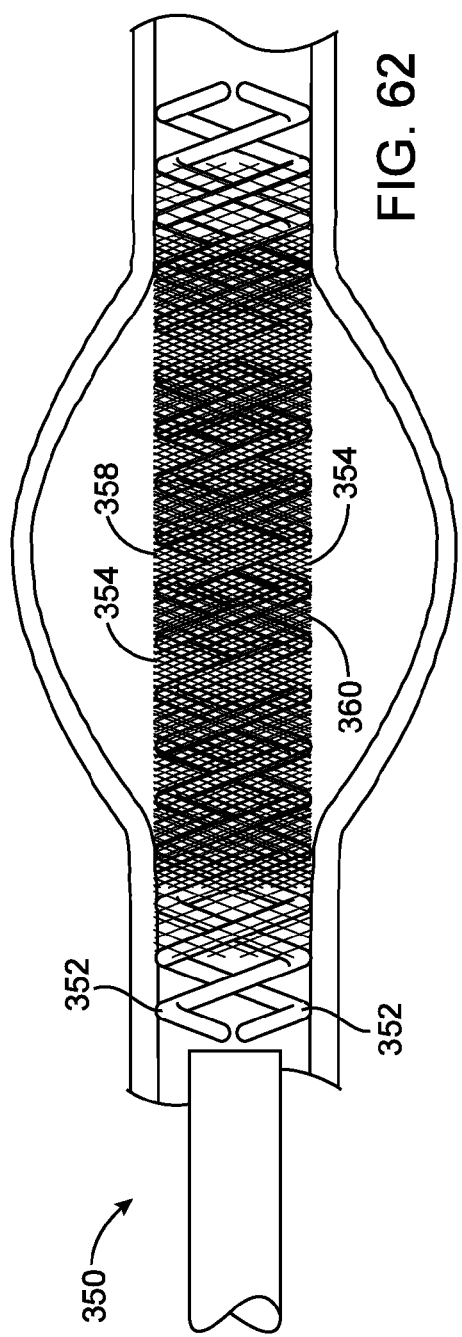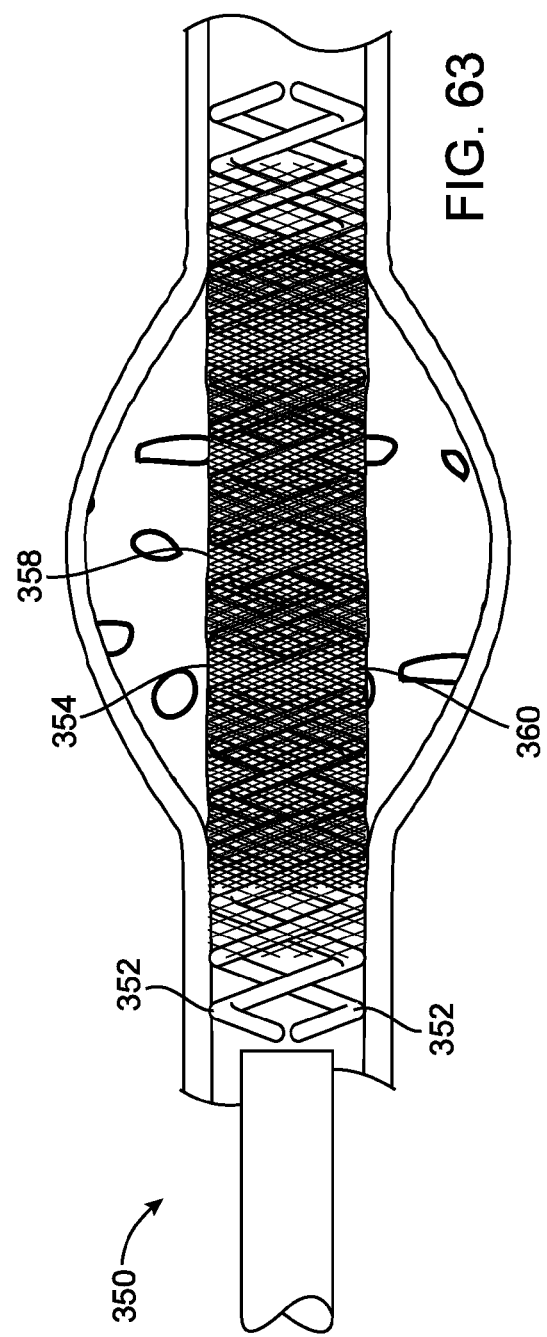

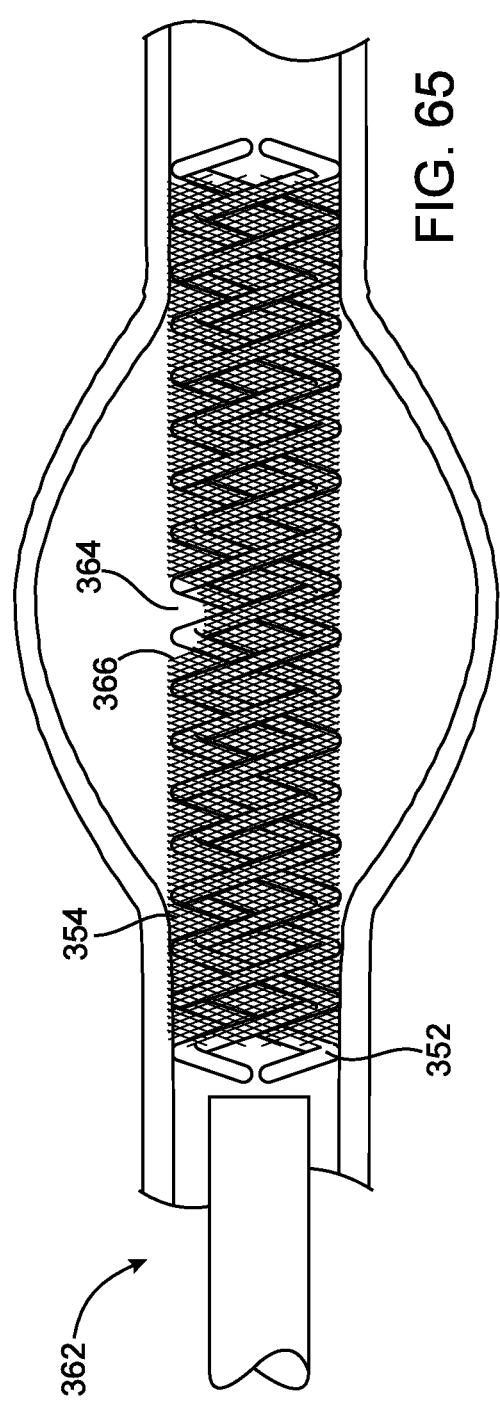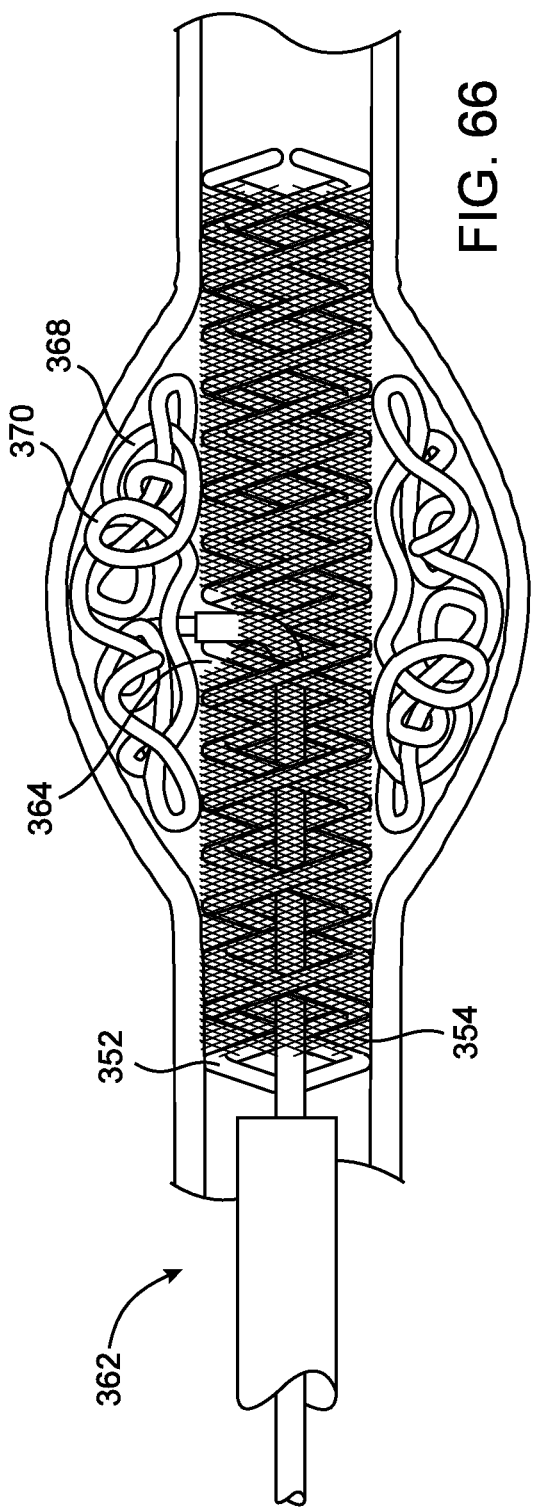

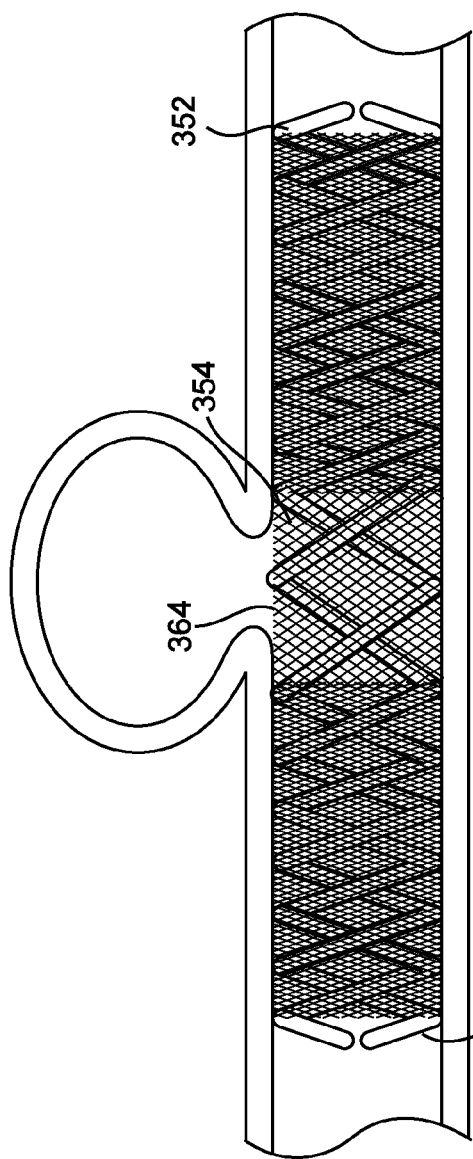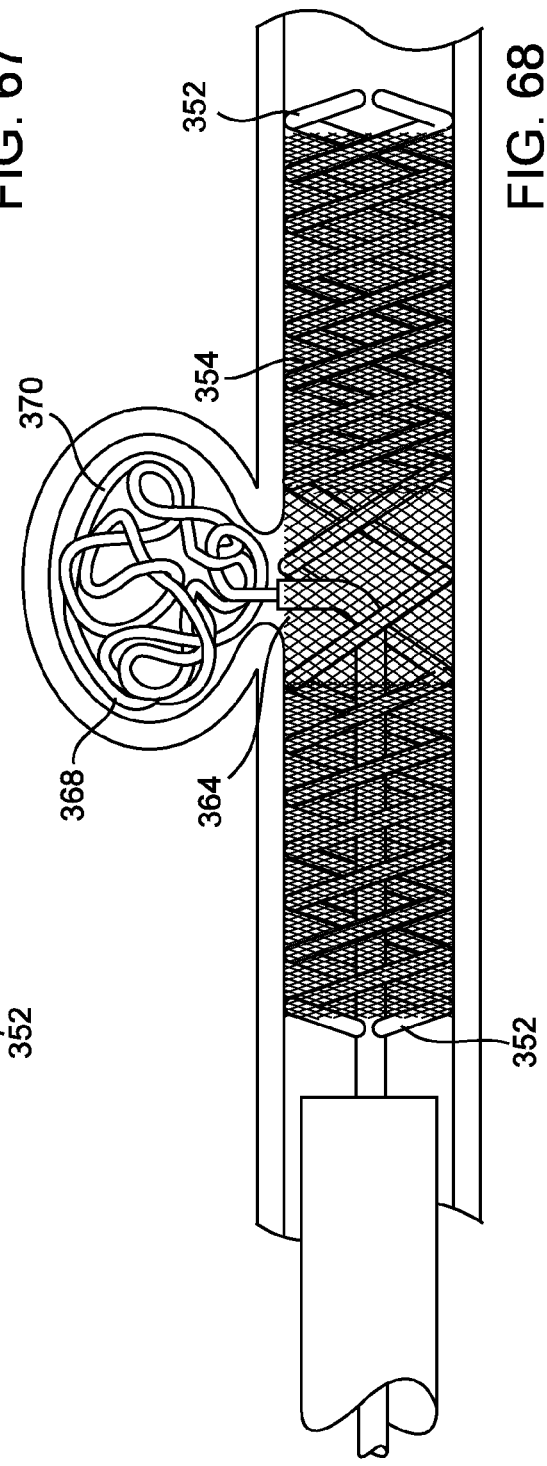

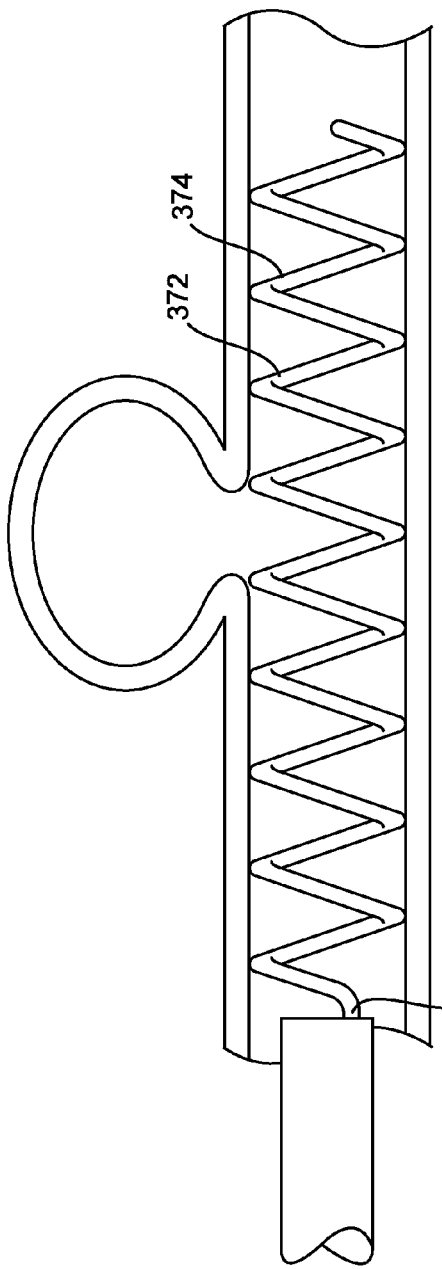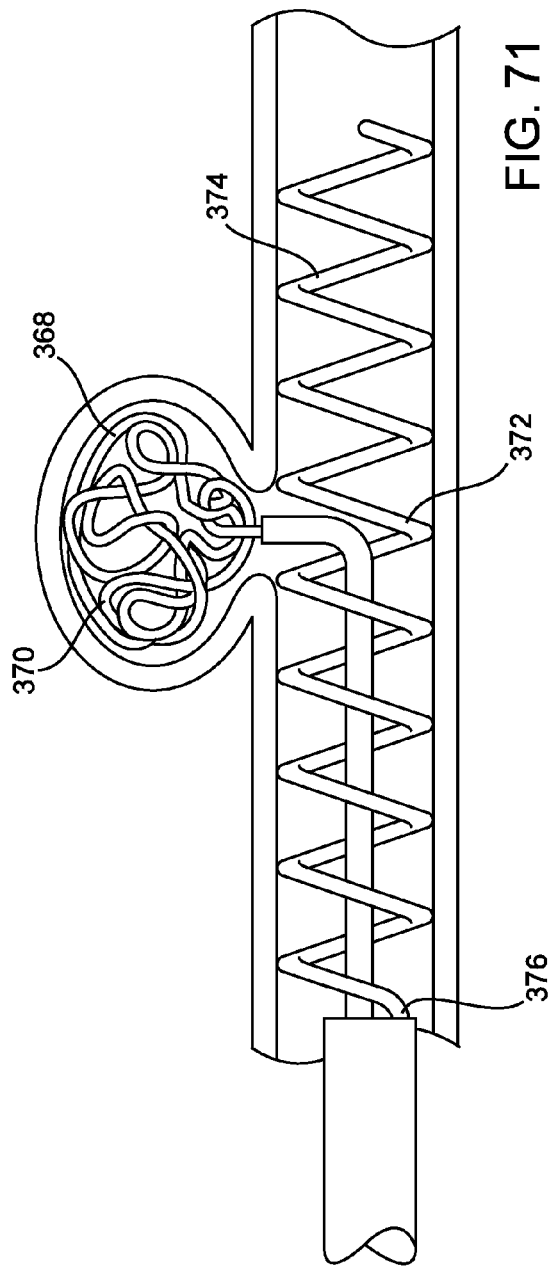

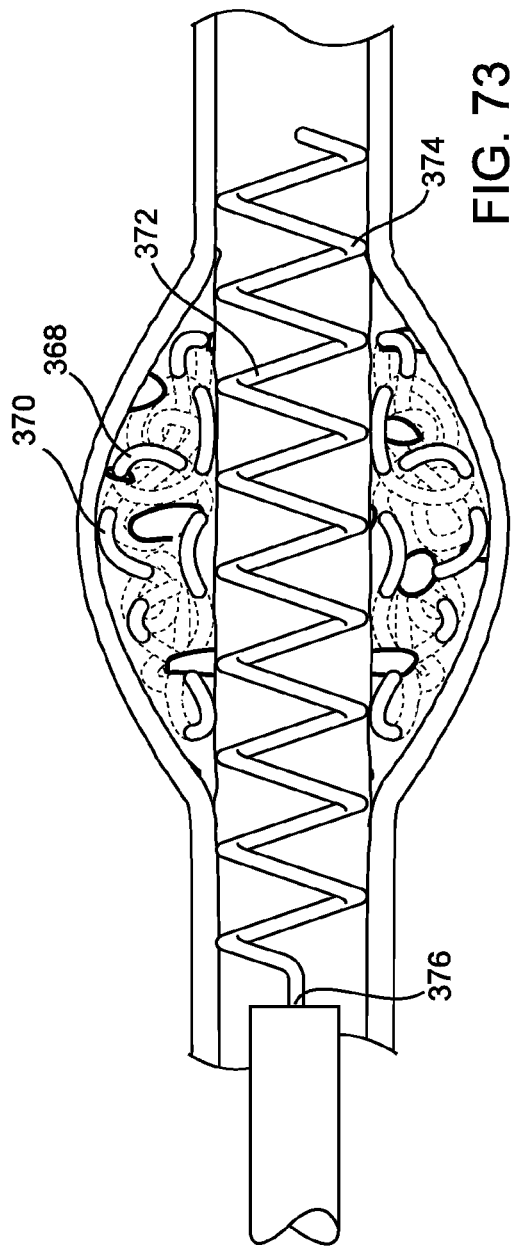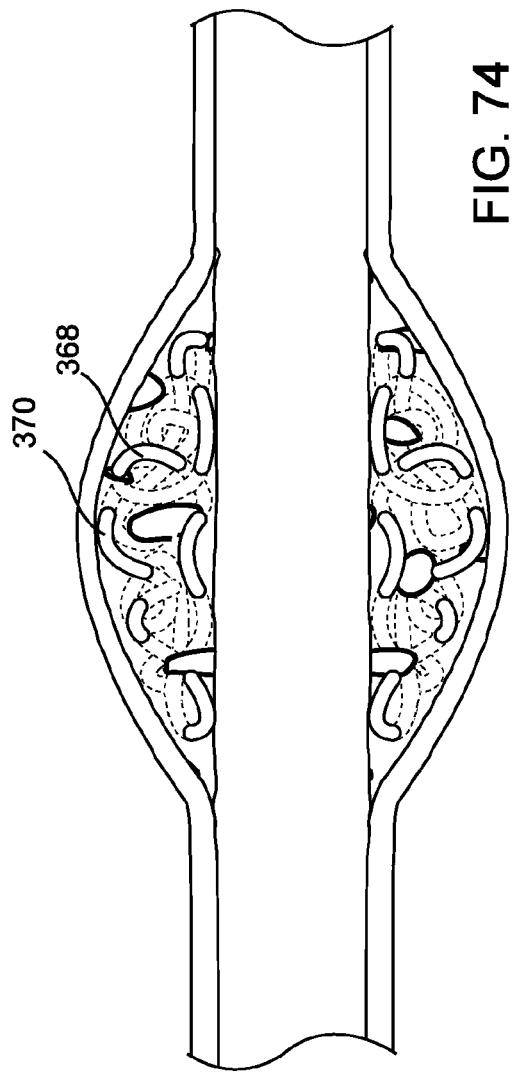

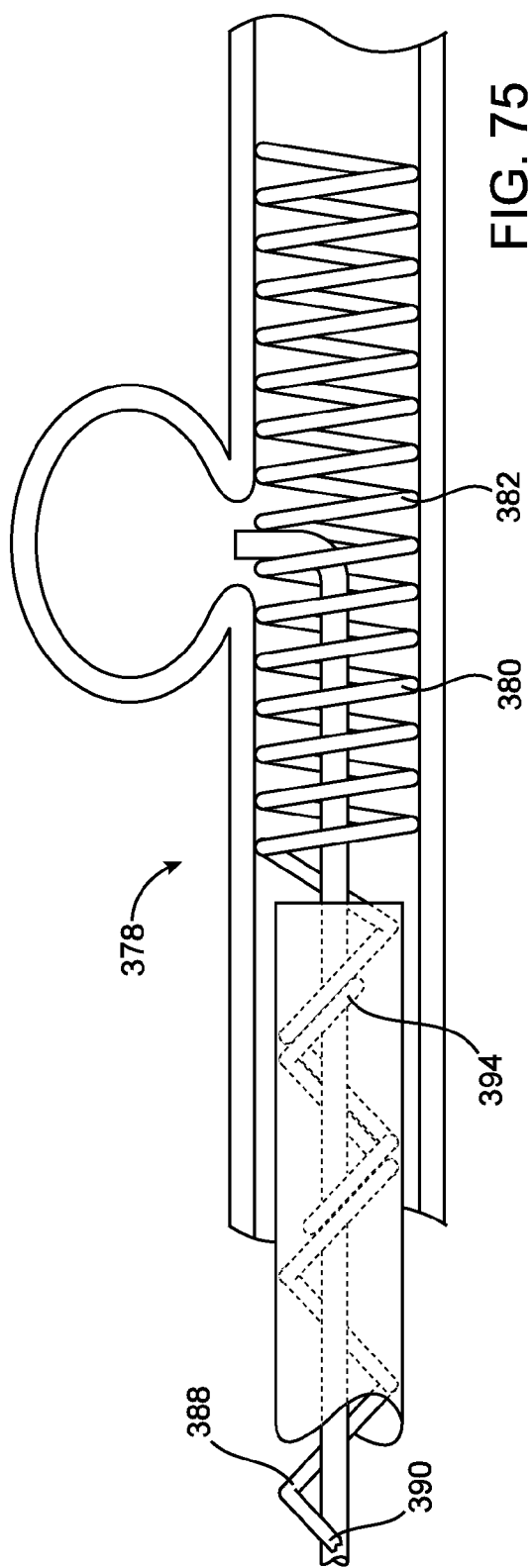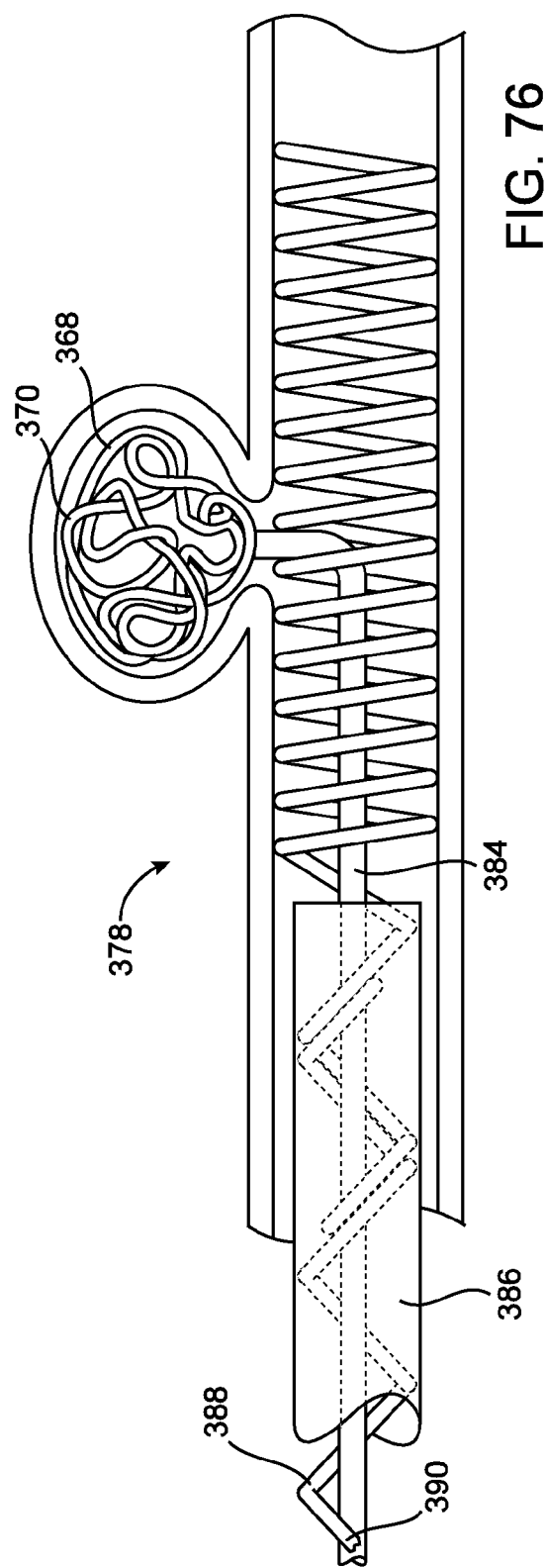

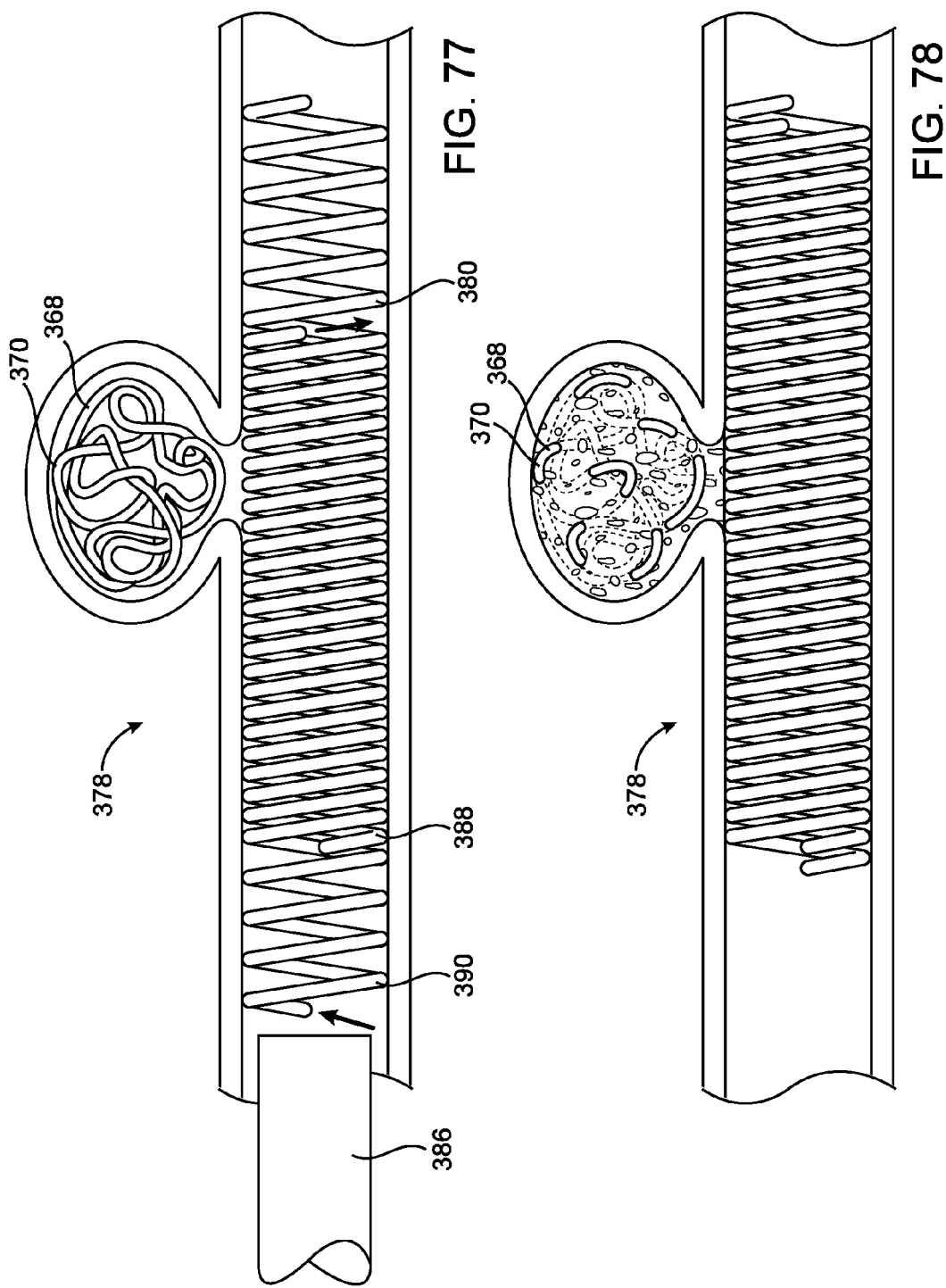

DEVICES AND METHODS FOR TREATING VASCULAR MALFORMATIONS

CROSS-REFERENCES TO RELATED APPLICATIONS

The present application is a continuation of U.S. application Ser. No. 12/653,821, filed on Dec. 21, 2009, which is a continuation of U.S. application Ser. No. 10/106,870, filed on Mar. 25, 2002, now abandoned which is a continuation-in-part of U.S. patent application Ser. No. 09/695,637, filed Oct. 24, 2000, now U.S. Pat. No. 6,746,468, which is a continuation in part of application Ser. No. 09/324,359 filed Jun. 2, 1999, now U.S. Pat. No. 6,375,668, all of which are hereby incorporated by reference.

BACKGROUND OF THE INVENTION

The present invention relates to treatment of abnormalities in a patient's vascular system. A specific use of the present invention described below is for the treatment of cerebral aneurysms although the various aspects of the invention described below may also be useful in treating other abnormalities such as arteriovenous malformations (AVM), hypervascular tumors, cavernous carotid fistulas, fibroid tumors, and non-reversible sterilisation via fallopial occlusion.

Cerebral aneurysms are enlargements of the cerebral vasculature, which protrude like a balloon from the wall of a cerebral artery. The cerebral aneurysm has a neck, which leads to the parental vessel and a body or "dome" which can vary in diameter from 1-30 mm.

The wall of the aneurysm is often weak and can rupture, leading to hemorrhage. Rupture of the aneurysm can kill the patient or leave the patient with permanent or transitory mental and physical deficits.

Aneurysms are often treated to prevent rupture, leading to hemorrhage, or to prevent rebleeding of acutely ruptured aneurysms. A conventional method of treating aneurysms is to fill the aneurysm with coils. The coils are introduced into the aneurysm one at a time through a delivery catheter until the aneurysm is filled. The aneurysm eventually becomes a solid mass of coils and thrombus.

A problem with the conventional method of using coils to fill aneurysms is that the aneurysm becomes a relatively solid mass due to coils and thrombus contained therein. The mass of coil and thrombus exerts pressure on adjacent areas of the brain, which may lead to other problems. Another problem with the conventional method is that the coils must be delivered one at a time into the aneurysm, which increases the procedure time and risk to the patient. For large aneurysms, up to twenty coils may be required to fill the aneurysm.

It is an object of the invention to provide improved methods and devices for treating aneurysms. These and other objects of the invention will become evident from the description of the preferred embodiments described below.

SUMMARY OF THE INVENTION

In a first aspect of the present invention, a method of treating an aneurysm is provided. An expandable structure is delivered through the vasculature in a collapsed position. Once the expandable structure is at the desired location, such as within a cerebral aneurysm, the expandable structure is expanded. The structure and advantages of the expandable structure are described below. The aneurysm wall is also reduced in size so that the aneurysm does not need to be completely filled in the conventional manner. The expandable shape is sized to be smaller than the aneurysm to permit reducing the size of the aneurysm by at least 30% percent.

A preferred method of reducing the size of the aneurysm is to heat the aneurysmal wall, preferably to a temperature of at least 60° and preferably 60-80° C., which causes the aneurysmal wall to shrink. The aneurysm may be heated in any suitable manner and preferred methods are monopolar and bipolar RF, laser, microwave, and simple electrical resistance heating. In a preferred method, electrical energy is delivered to the expandable device itself to generate heat. A fluid may be introduced into the aneurysm to prevent clotting during heating and to provide thermal and/or electrical conductance. When using RF heating, for example, the fluid may be saline and more preferably hypertonic saline. Although it is preferred to heat the aneurysmal wall to reduce the size of the aneurysm, the aneurysm may also be reduced in size by chemical action.

The expandable structure forms a matrix of filaments in the expanded condition. The matrix preferably forms a woven or braided structure, however the filaments may also be randomly oriented, parallel, or non-intersection filaments. The matrix may be flexible filaments, such as platinum ribbon, extending randomly, radially or helically within an expandable, permeable, mesh-like enclosure. The material may also be an expandable material such as polymer, nitinol, stainless steel, tungsten or tantalum and alloys/composites thereof.

The expandable device preferably fills a volume of at least 10% of the aneurysm volume, more preferably at least 40% and most preferably at least 60% of aneurysm volume. The expandable device preferably has internal filaments within the volume to quickly form a stable thrombus. An advantage of the expandable device is that a three-dimensional structure forms without requiring separate delivery of a cage and coils as described in International Application WO 99/07293. In another aspect, the expandable device has a deforming portion, which plastically deforms when moving to the expanded position. The deformable portion holds the flexible filaments in the expanded position.

The aneurysm may be reduced in size until the aneurysmal wall contacts the expandable structure so that the expandable structure supports and reinforces the aneurysmal wall. In a particularly advantageous embodiment of the invention, the expandable structure itself is used to transmit energy to heat the aneurysmal wall, which causes the aneurysmal wall to fuse to the expandable structure, thereby reinforcing the aneurysmal wall and preventing migration of the expandable structure into the parental vessel.

In another aspect of the invention, the aneurysmal wall may be reduced in size together with the expandable device. In a preferred embodiment, the expandable structure is a soft mesh, which easily collapses when the aneurysmal wall is shrunk.

Various optional steps and structure may also be provided. For example, a sealant may be delivered into the aneurysm to ensure that the aneurysm is isolated from the parental artery. An advantage of the present invention is that the sealant is held within a matrix formed by the expandable device, which holds the sealant in the aneurysm.

The proximal portion of the expandable structure may be insulated to protect the neck of the aneurysm. The insulation may coat only the flexible filaments so that the structure is still permeable to fluid. Alternatively, the insulation may be impermeable to protect the neck from hot fluid slowly expelled into the aneurysm or to isolate the aneurysm entirely from the parental vessel.

The expandable device may have one or more expandable sections. In an embodiment, the expandable device has two expandable sections wherein energy is delivered to the dome with one of the sections while the second section is insulated to protect the neck.

The expandable device may have a locking mechanism for locking the expandable device in the expanded position. The expandable device is naturally biased toward the collapsed position so that the operator may partially deploy the expandable device to determine whether the device has the appropriate size. If the device does not have the appropriate size, the device is collapsed and removed and another device having the appropriate size is introduced. The locking mechanism is then actuated when the user is satisfied with the size of the device.

In still another aspect of the present invention, a catheter has a cover, which is positioned over the neck of the aneurysm to isolate the aneurysm from the parental vessel. The aneurysm is then reduced in size as explained above while the cover isolates the aneurysm. The cover also protects the patient from hemorrhage by isolating the aneurysm from the parental vessel. The cover may be periodically moved to expel heated fluid into the parental vessel when heating and shrinking the aneurysm.

In yet another aspect of the present invention, a coil is used to cover the neck of the aneurysm to regulate the flow of hot fluid out of the aneurysm and into the parental vessel. The pitch of the coil can be varied by the operator during deployment to allow faster or slower leakage of hot fluid out of the aneurysm and into the parent artery during heating.

A catheter is also provided which has a low-impedance coil, such as flat copper ribbon or other suitable material, disposed in the catheter tip. Upon infusion of saline through the catheter and passage of RF energy through the coil, the saline is heated and conducts electrical energy to heat the fluid.

These and other aspects and advantages of the invention will become evident from the following description, drawings and claims.

Still another device for treating an aneurysm is provided which has a cover, which covers the neck of the aneurysm to isolate the aneurysm from a parental vessel. The device also has a lateral extension, which is coupled to the cover and extends into the aneurysm when the cover is positioned over the neck of the aneurysm.

The cover is preferably a mesh and the lateral extension preferably forms 1-8 loops. The cover is preferably a substantially flat element, which is positioned against a wall of the parental vessel around the neck of the aneurysm. The cover preferably extends no more than about 180 degrees around a longitudinal axis of the device when expanded so that branch vessels are not occluded by the cover. The extension is preferably expandable with one end connected to the cover and the other end sliding relative to the cover to permit the extension to expand and contract.

The present invention describes still another device for treating an aneurysm, which has the cover for covering the neck of an aneurysm. The cover is mounted to an expandable element and is covered by a retractable sheath. The sheath is preferably folded over itself at the distal end so that the cover is exposed as the sheath is pulled back over itself. The cover is preferably wrapped around the expandable member without overlapping folds, flaps or sections. The cover is preferably adhered to the parental vessel wall in any suitable manner such as with an adhesive. The cover may be a sheet of material or a metallic frame having impermeable layer attached thereto.

Yet another device for treating an aneurysm is provided which has a plurality of filaments extending between proximal and distal hubs. The filaments preferably form a generally concave surface, which covers a neck of an aneurysm when positioned in the aneurysm. The device may also have a concave side opposite the convex side. The filaments form overlapping loops when viewed along an axis through the hubs. The filaments are preferably in a relatively straight configuration when advanced through the delivery catheter to the aneurysm.

Still another device for treating an aneurysm has a plurality of filaments, preferably 2-4 filaments, with the proximal ends of the filaments being coupled together and the distal end of the filaments being free. Each of the filaments preferably forms a coil in the expanded position. The coils may have a central axis generally lying in the same plane.

In another aspect of the present invention, a device for treating a vascular malformation includes first and second vascular elements. The first vascular element is delivered to a vascular malformation and an embolic material is then delivered through the first vascular element and into the vascular malformation. The embolic material may be delivered through a lumen extending through the first vascular element. The second vascular element is then moved into the vascular malformation to fill interstitial spaces or voids in the first vascular element. The first and second vascular elements may be coupled to one another so that the second vascular element is guided by the first vascular element into position.

In still another aspect of the present invention, a temporary vascular element may be delivered to the vascular malformation. An embolic material may then be delivered through the vascular element with the vascular element helping to retain the embolic material in the malformation. The vascular element also helps to reduce blood flow in the malformation to induce thrombosis. After a period of time to permit thrombosis, the vascular element is removed.

In yet another aspect of the present invention, a vascular element is provided which has a main coil and a plurality of secondary windings. In one example, the device has two main coils wound in opposite directions and interwoven. The device may have an increased density of the main coil or secondary windings at a central portion. Alternatively, the device may have a side opening through which embolic materials may be delivered. The side opening may extend circumferentially around the device or may be a cutout along a portion of the circumference. The side opening may be provided by an absence of the main coil and/or secondary windings or may simply be provided by an increased spacing between the coils and/or windings.

BRIEF DESCRIPTION OF THE DRAWINGS

FIG. 2 shows an expandable device in a collapsed position.
FIG. 3 is a perspective view of the expandable device with the mesh removed.

FIG. 16 shows a heating device.

FIG. 17 shows a heating device with the tip curved.

FIG. 24 shows a catheter having a cover for isolating an aneurysm from the parental vessel.

FIG. 25 is a cross-section of the catheter of FIG. 21 along line A-A.

FIG. 62 shows another device for treating a vascular malformation.

FIG. 63 shows the device of FIG. 62 with a thrombus formed in the malformation.

FIG. 65 shows still another device for treating a vascular malformation.

FIG. 66 shows the device of FIG. 65 with an embolic material delivered through the device.

FIG. 67 shows yet another device for treating a vascular malformation.

FIG. 68 shows the device of FIG. 67 with an embolic material delivered through an opening in the device.

FIG. 70 shows a device for treating a vascular malformation.

FIG. 71 shows an embolic element delivered into the malformation.

FIG. 73 shows another device for treating a malformation with a temporary vascular element deployed.

FIG. 74 shows a thrombus formed in the aneurysm after removal of the device of FIGS. 72 and 73.

FIG. 75 shows another device for treating a malformation with a first element positioned at the malformation.

FIG. 76 shows an embolic element delivered through the first element and into the malformation.

FIG. 77 shows delivery of a second element.

FIG. 78 shows a thrombus formed in the malformation using the first and second elements of FIGS. 76 and 77.

DESCRIPTION OF THE PREFERRED EMBODIMENTS

Figure 1:
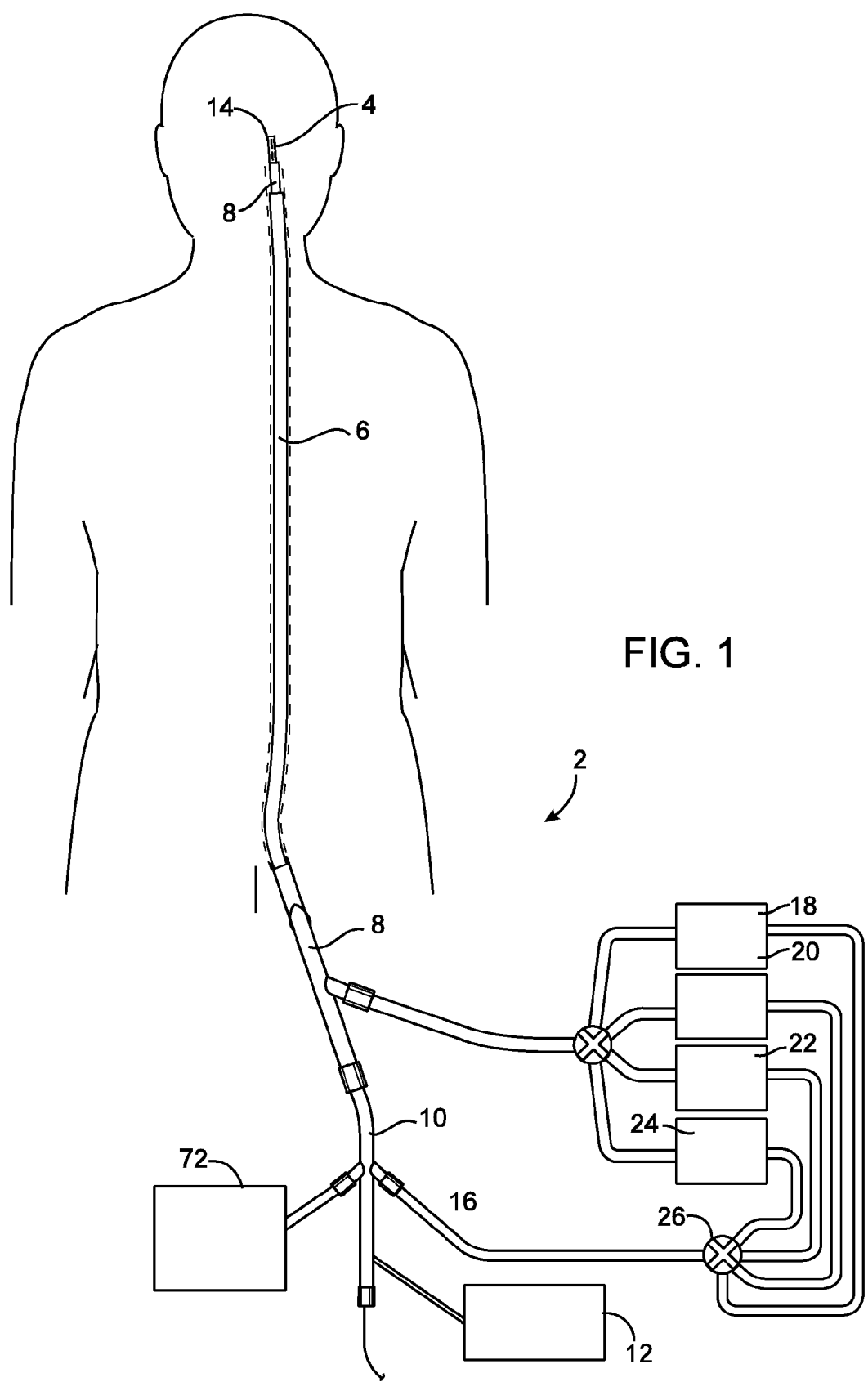
FIG. 1 is a system for treating a patient's vascular system.

Referring to FIG. 1, a system 2 for introducing an expandable device 4 into a cerebral aneurysm is shown. A first catheter 6 extends through a penetration in the femoral artery and up to the carotid artery. A second catheter 8 is advanced through the first catheter 6 and into the cerebral vasculature to the site of the aneurysm or other abnormality. A delivery catheter 10 is then advanced through the second catheter 8. The catheter 10 delivers an expandable device 4 which partially fills the aneurysm as will be described below. The system 2 also has an energy supply 12 for heating the aneurysm to shrink the aneurysm as will be described below.

Figure 6:
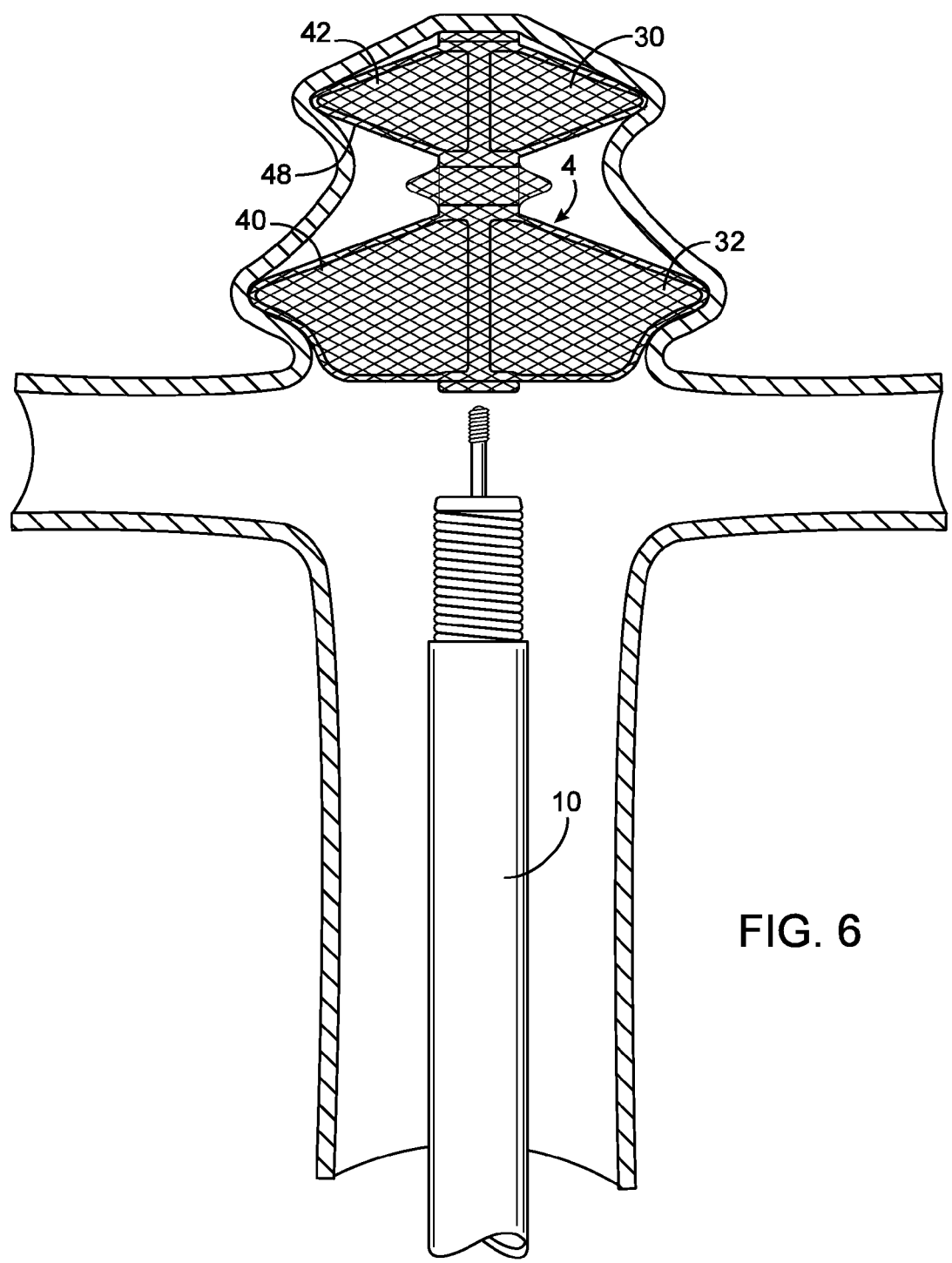
FIG. 6 shows the expandable device detached from the delivery catheter.

After the expandable device 4 has been delivered to the aneurysm and expanded, the aneurysm is reduced in size as shown in FIG. 6. The aneurysm may be shrunk partially toward the expandable device 4, into engagement with the expandable device 4, or may even be shrunk until the expandable device 4 is also reduced in size. An advantage of shrinking the aneurysm is that the aneurysm does not need to be completely filled with coils in the conventional manner. The conventional method of filling the aneurysm with coils creates a relatively solid mass in the aneurysm which can press against adjacent structures leading to further problems. The expandable device 4 is removably mounted to the end of a shaft 5 in the manner described below so that the expandable device 4 may be released in the aneurysm. The expandable device may be released with a mechanical mechanism, a thermoadhesive bond, or an electrolytically or chemically severable bond.

The aneurysm may be shrunk in any suitable manner and a preferred method is to heat the aneurysmal wall. Shrinking of the aneurysm may also be accomplished through chemical action. The aneurysmal wall is preferably heated to a temperature of 60-80° C. and preferably at least 70° C. Depending upon the size of the aneurysm, the aneurysmal wall is preferably heated for at least 10 seconds and generally between 10 seconds and 5 minutes.

In the preferred system of FIG. 1, the energy supply 12 supplies RF energy to heat and shrink the aneurysm. The expandable device 4 is preferably configured as a mono-polar RF electrode 14 and the energy supply 12 is preferably an RF generator. A suitable second electrode (not shown) is placed in contact with the patient's skin in the conventional manner. The aneurysm may, of course, be heated with the energy supply being a hot fluid, laser, microwave, bi-polar RF or a resistance heating device without departing from the scope of the invention.

Figure 4:
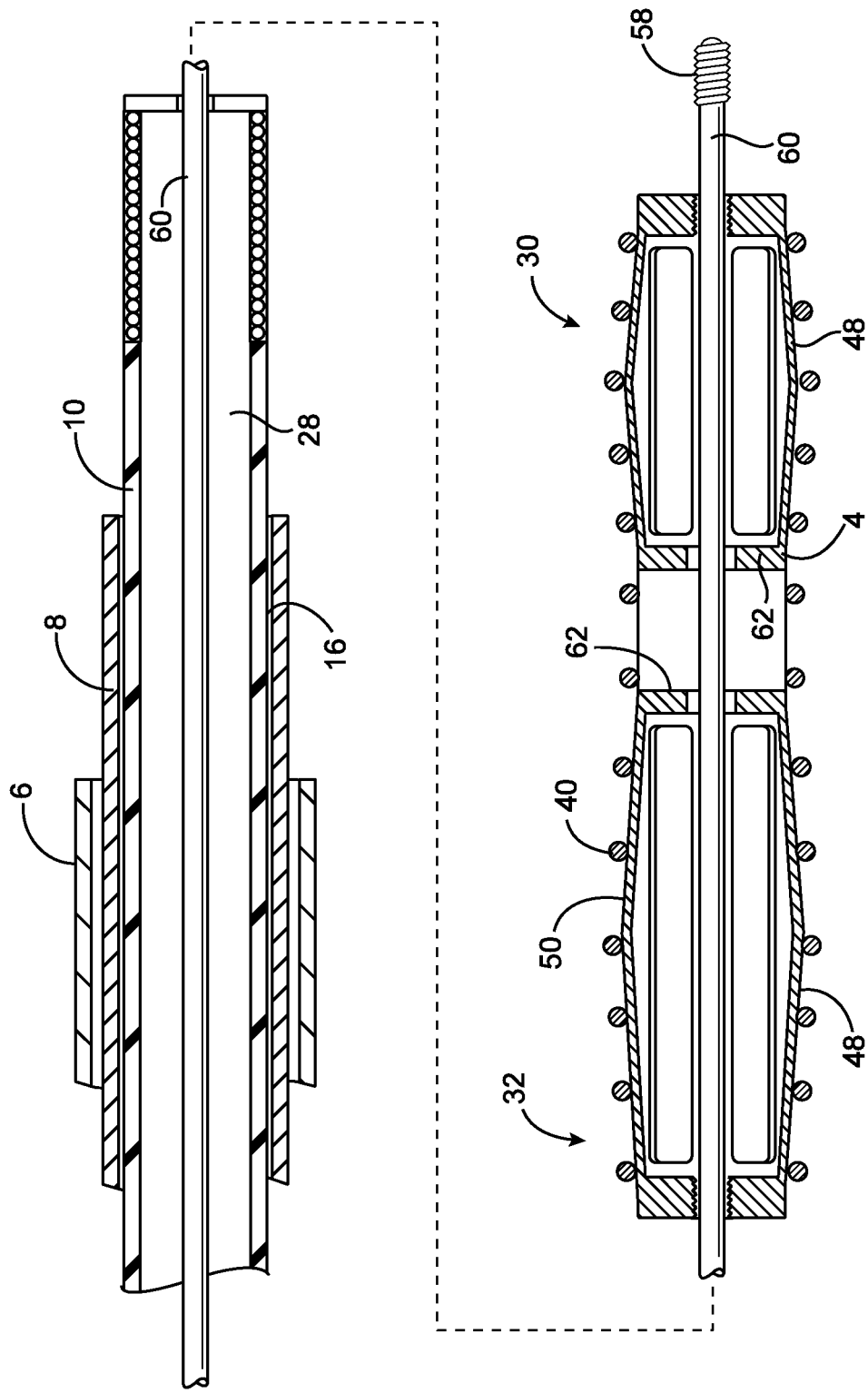
FIG. 4 is a cross-sectional view of the expandable device.

Referring to FIGS. 1 and 4, the catheter 8 has a lumen 16 coupled to a source of fluid 18 which is preferably a conductive fluid such as saline and more preferably hypertonic saline. The lumen 16 may also be coupled to a source of sealant 20 which may be used to seal the aneurysm as described below. The sealant may be any suitable sealant such as cyanoacrylates, ethylene vinyl-alcohol, cellulose acetate polymers, fibrin glues and other liquid-type tissue sealants. The sealants may also be bioperodable and/or bio-absorbable. The lumen 16 is also coupled to a vacuum source 22 for suctioning fluids and reducing the size of the aneurysm. A source of contrast 24 is also provided for visualization of the aneurysm, vasculature and device positions. A valve 26 couples the lumen 16 to the various sources 18, 20, 22, 24. The delivery catheter 10 also has a lumen 28 which may be coupled to the sources 18, 20, 22, 24 and discussion of use of the lumen 16 is equally applicable for the lumen 28.

Figure 5:
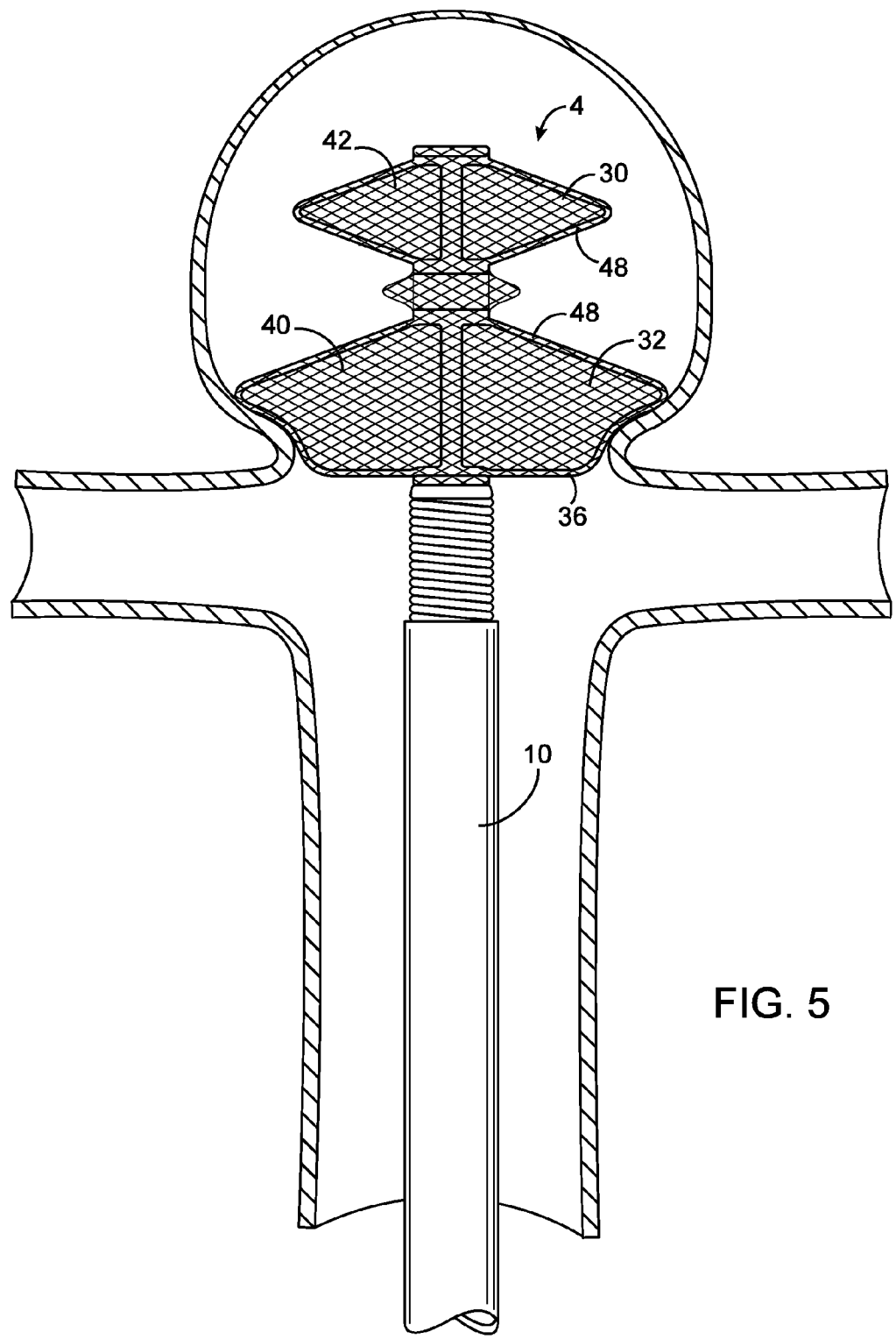
FIG. 5 shows the expandable device in an aneurysm.

Referring to FIGS. 2, 3 and 5, the expandable device 4 has first and second expanding sections 30, 32. Although it is preferred to provide both the first and second expanding sections 30, 32, the expandable device 4 may include only one expanding section or three or more expanding sections without departing from the scope of the invention. The first section 30 acts as the electrode 14 to deliver RF energy from the energy source 12 to the aneurysm. The second section 32 is insulated and does not transmit energy to the aneurysm so that the neck of the aneurysm is protected. The second section 32 is preferably coated with PTFE, polyamide, FED, or PFA to prevent RF energy transmission. Protecting the neck of the aneurysm also protects peripheral vessels adjacent the neck of the aneurysm.

Figure 9:
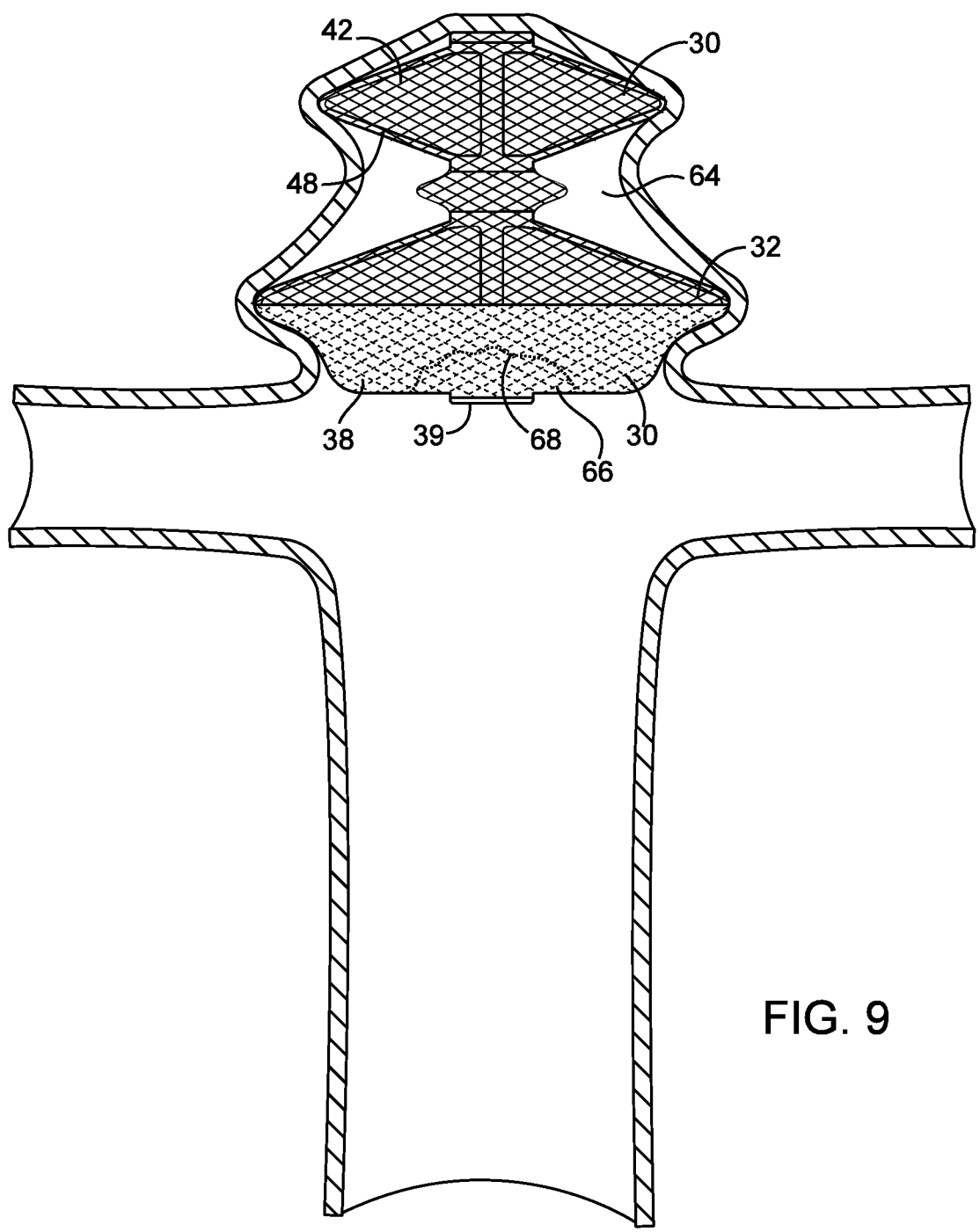
FIG. 9 shows the expandable device having a proximal portion, which is relatively impermeable to the sealant so that the sealant is retained in the aneurysm.

The second expandable section 32 may be permeable to fluid so that heated fluid in the aneurysm may be slowly expelled into the parental vessel to dissipate heat. The second section 32 may also have a fluid impermeable portion 36 adjacent the neck to further protect the neck of the aneurysm as shown in FIG. 9. The fluid impermeable portion 36 is preferably a flexible sheath 38 having a ring or annular shape. The ring shape may interrupt at a radially inner portion 39 so that heated fluid may still be slowly expelled into the parental vessel. Alternatively, the sheath 38 may completely isolate the aneurysm from the parental vessel.

The first and second expandable sections 30, 32 have a number of flexible filaments 40 which move from the collapsed position of FIG. 2 to the expanded position of FIG. 5. The flexible filaments 40 are preferably woven or braided to form a substantially closed-form mesh structure 42 in the expanded position. The filaments 40 and mesh 42 have the characteristics described below and are graphically depicted in the drawings for clarity. A preferred mesh structure 42 is also described with reference to FIG. 34 below.

Referring again to FIGS. 2 and 3, the filaments 40 are positioned over deformable elements 48 which hold the flexible filaments 40 in the expanded position. Referring to FIG. 3, the deformable elements 48 have columns 50 extending between collars 52, 53 at the ends. The deformable elements 48 are formed from tubes which have four cut-out sections 54 to form the columns 50. The collars 52 are then attached to the ends of the tube. The columns 50 are bent outward slightly so that they will buckle outwardly when compressed. As will be described in further detail below, the deformable elements 48 are plastically deformed when moving to the expanded position to hold the filaments 40 in the expanded position. The columns 50 may also be designed with curved or sinusoidal shaped sections to improve flexibility.

Referring to FIG. 4, the proximal and distal collars 52 are threaded to engage a threaded tip 58 of a guidewire 60 for manipulating the expandable device 4. Intermediate collars 62 provide only throughholes to hold and guide the expandable device 4 on the guidewire 60. When expanding the device 4, the guidewire 60 is pulled until the device 4 is trapped between the delivery catheter 10 and the threaded tip 58. The guidewire 60 is then rotated to engage the tip 58 with the distal threaded collar 52. When the tip 58 is threaded into engagement with the distal collar 52, the guidewire 60 can be pulled to expand the device. When the device 4 is partially expanded, the deformable elements 48 may still be within their elastic range so that the expandable device 4 will recover the collapsed position when tension is released on the guidewire 60. The operator may then check to see if the device 4 has the appropriate size and shape for the aneurysm before fully deploying the device. If the operator determines that the device 4 is too small or too large, the device 4 is collapsed and removed and another expandable device of appropriate size advanced to the aneurysm.

When the operator is ready to deploy the device 4, the operator pulls the guidewire 60 so that the deformable elements 48 undergo plastic deformation and move to the expanded position. Even if the device 4 is moved to the expanded position, the operator may still retrieve the device by engaging the proximal collar 53 with the threaded tip 58 and withdrawing the device into the second catheter 8.

After the expandable device 4 has been moved to the expanded position, the aneurysm is then preferably reduced in size. In a preferred method, RF energy is delivered to the first expandable section 30 through the guidewire 60 and a conductive fluid, preferably hypertonic saline, is injected into the aneurysm through the lumen 16 or lumen 28. FIG. 6 shows the aneurysm reduced in size until the aneurysm engages the first section 30. The threaded tip 58 is then disengaged from the device 4 leaving the device 4 in the shrunken aneurysm.

Figure 7:
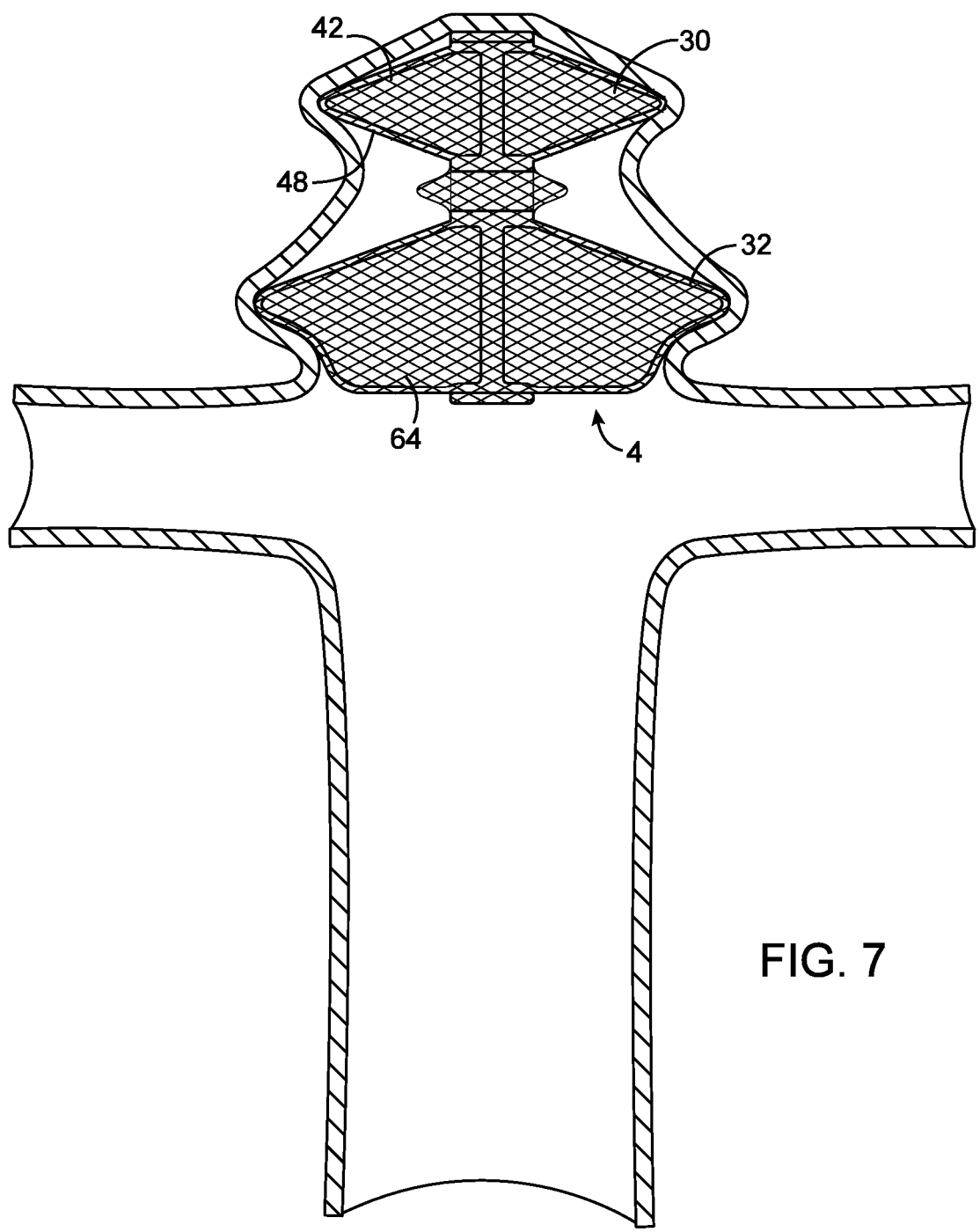
FIG. 7 shows the expandable device of FIG. 6 with a sealant introduced into a portion of the expandable device.
Figure 8:
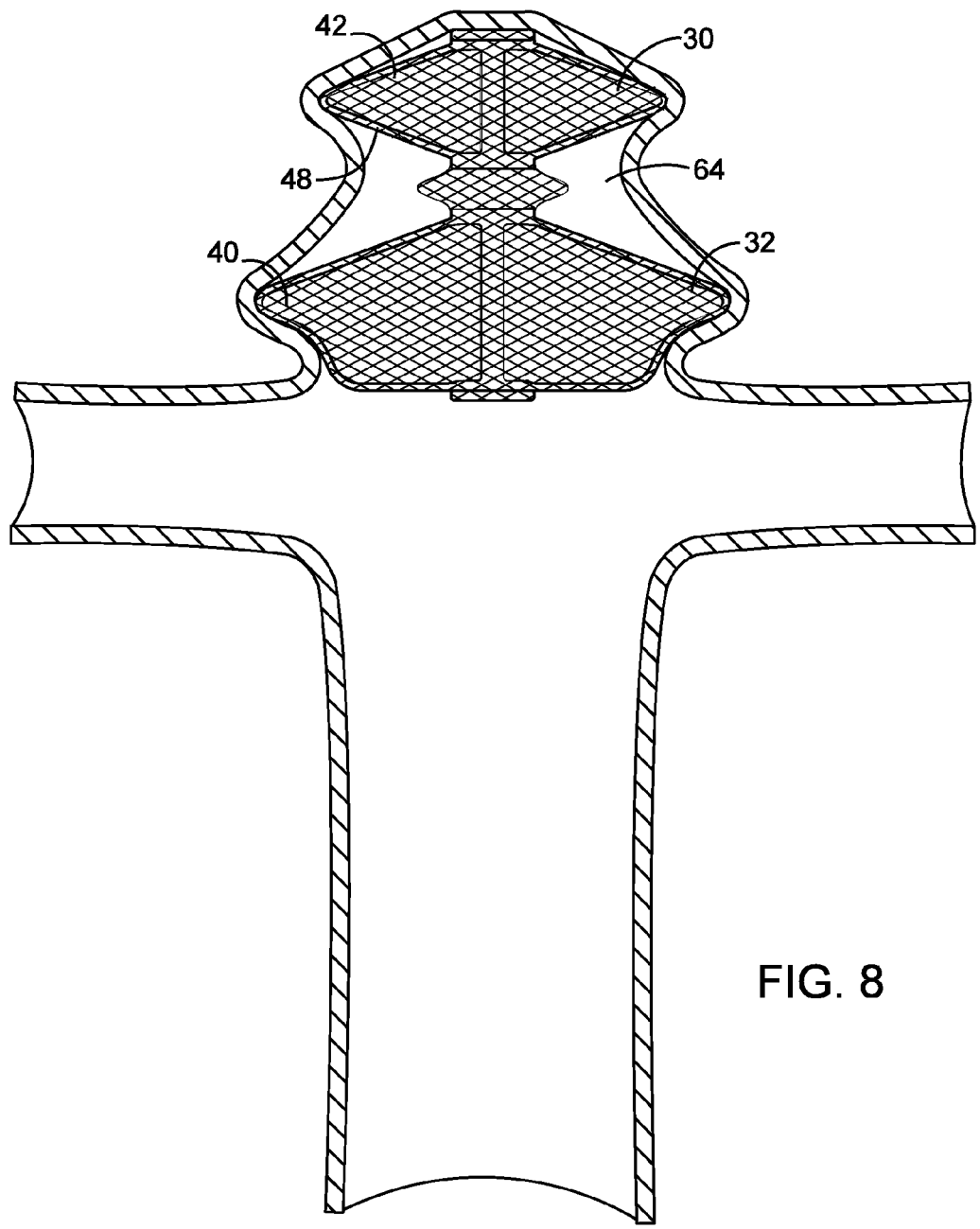
FIG. 8 shows the sealant filling the aneurysm and the expandable device.

As an optional step, the sealant 64 from the source of sealant 20 may also be introduced into the entire aneurysm (FIG. 8) or into just the second section 32 (FIG. 7) to seal the aneurysm. An advantage of the present invention over conventional methods is that the sealant 64 is contained within the closed-form mesh structure 42 to prevent escape of the sealant 64 into the parental vessel. Referring to FIG. 9, a proximal portion 66 may be impermeable to further isolate the aneurysm from the parental vessel. A small amount of the sealant 64 may also be delivered to completely isolate the aneurysm if necessary as shown at dotted-line 68. The method of the present invention described above may, of course, be practiced with any suitable structure other than the structure of FIGS. 1-9 without departing from the scope of the invention.

Referring to FIGS. 11-15, another delivery catheter 70 is shown for use with the system of FIG. 1. The delivery catheter 70 is delivered through the first and second catheters described above. The catheter delivers an expandable device 4A to the aneurysm through the second catheter 8 (see FIG. 1).

The delivery catheter 70 has an expandable member 72, preferably a balloon 74, for deploying the expandable device 4A. The device 4A is configured to retain the expanded position of FIG. 12 after the balloon 74 has been deflated. The delivery catheter 70 has an inflation lumen 72 coupled to a source of inflation fluid 74 for inflating the balloon (FIG. 1).

The expandable device 4A is preferably made of a number of flexible filaments 76. The filaments 76 are preferably woven or braided but may also be a number of non-woven filaments. The filaments 76 may be any suitable material and a preferred material is platinum alloy (92% platinum, 8% tungsten) wire having a thickness of 0.005-0.003 inch.

Figure 12:
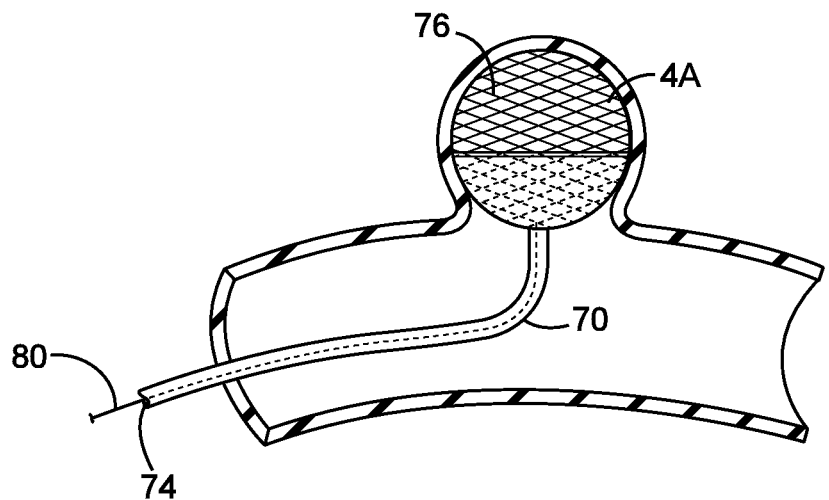
FIG. 12 shows the expandable device of FIG. 11 in an expanded position.
Figure 13:
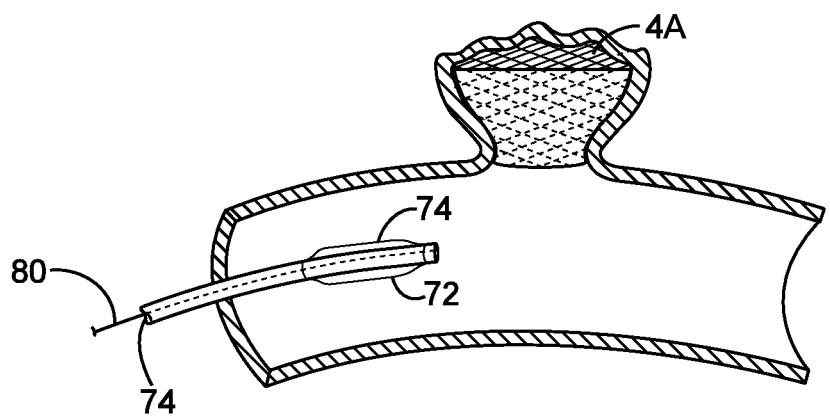
FIG. 13 shows the expandable device reduced in size and the expandable device having a proximal portion, which is insulated to protect the neck of the aneurysm.

The expandable device 4A may take any shape and may have a number of predetermined shapes which can be selected depending upon the shape of the aneurysm and the nature of the patient's vasculature. Referring to FIG. 12, the expandable device 4A has a simple spherical shape. Although the expandable device 4A is shown as spherical, the expandable device 4A preferably has a width to height ratio of more than 1.1, more preferably at least 1.2 and most preferably at least 1.8. The width and height are defined relative to the aneurysm (FIG. 12) and/or relative to a longitudinal axis 76 of the expandable device 4A. The preferred dimensions provide a relatively large width so that the expandable device 4A cannot escape through the neck of the aneurysm after expansion. The height of the expandable device 4A provides clearance for shrinking the aneurysmal toward the expandable device. The width to height ratios are preferred dimensions for all of the embodiments described herein.

Once the expandable device 4A has been delivered to the aneurysm, the aneurysm is preferably reduced in size in any manner described herein. A method of reducing the size of the aneurysm is to deliver energy to the expandable device 4A from the energy source 12. The energy may be delivered to the aneurysm by delivering RF energy to the expandable device 4A with one or more wires 80 passing through the second catheter 8. During RF delivery, the second catheter 8 may be used to deliver fluid, such as hypertonic saline, to the aneurysm.

Figure 14:
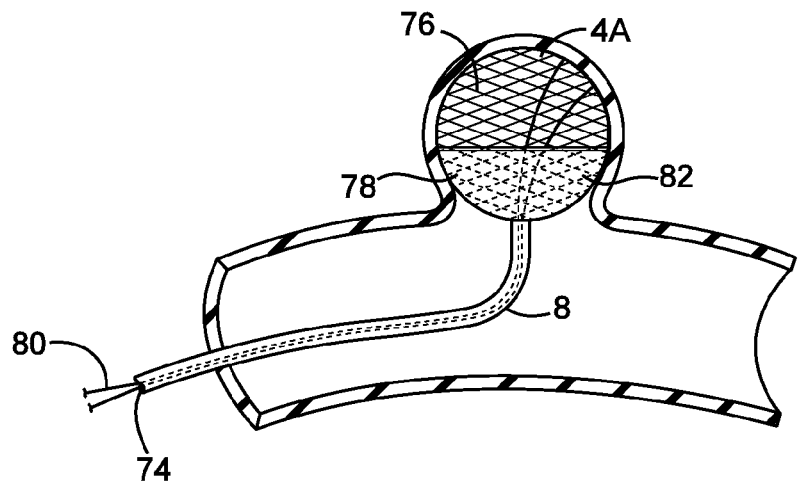
FIG. 14 shows the expandable device of FIG. 11 with simple resistance heating used to shrink a portion of the aneurysm into contact with the expandable device.
Figure 15:
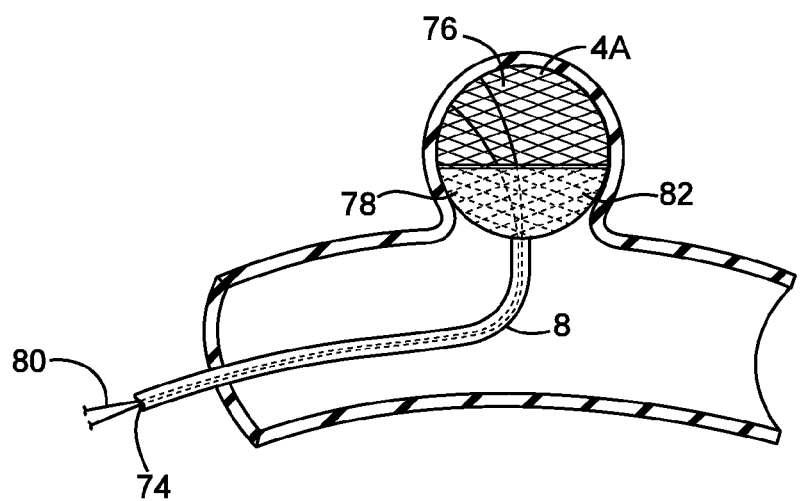
FIG. 15 shows the use of simple resistance heating to shrink another portion of the aneurysm into contact with the expandable device.

Referring to FIGS. 14 and 15, simple resistance heating may also be used by moving the wires 80 into contact with the expandable device 4A to conduct electricity therebetween as shown in FIG. 14. An advantage of the system is that different portions of the aneurysm can be heated to shrink the aneurysm as shown in FIGS. 14 and 15.

The expandable device 4A may be insulated at a proximal portion 82 so that energy is delivered to the aneurysm dome rather than toward the neck and parental artery. The flexible filaments 76 may be coated with any suitable insulation, such as paraline, and may be applied by spraying, dipping or etching. The expandable device 4A may also have the flexible sheath 78 over the insulated region to further shield the neck of the aneurysm.

Referring to FIG. 16, a heating device 84 is shown which may be used to heat and shrink the aneurysm. The heating device 84 is advanced into the aneurysm to heat fluid in the aneurysm thereby heating and shrinking the aneurysmal wall. Two insulated wires 86, 88 are wrapped around a core wire 90 and covered with a sheath 92 along the proximal portion. The sheath 92 forms a lumen 94 therethrough which may be coupled to the various sources 18, 20, 22, 24 described above with connector 96. The distal end of the wires 86, 88 form proximal and distal electrodes 98, 100 for bipolar RF heating. The core wire 90 is attached to the distal electrode 100.

An actuator 102 is manipulated to change the distance between the electrodes 98, 100 and to bend the tip in the manner shown in FIG. 17. The actuator 102 is coupled to the core wire 90. The device may be configured so that the electrodes 98, 100 move toward another when the actuator 102 is manipulated, or the device may be configured so that the tip curves as shown in FIG. 17. The tip may be curved to navigate tortuous vessels and may be curved during heating. In use, the distal end of the device 84 is introduced into the aneurysm and the actuator 102 is manipulated to curve the distal end. RF energy is then delivered and a fluid, such as hypertonic saline, is delivered through the second catheter 8 or through the lumen 94.

Figure 18:
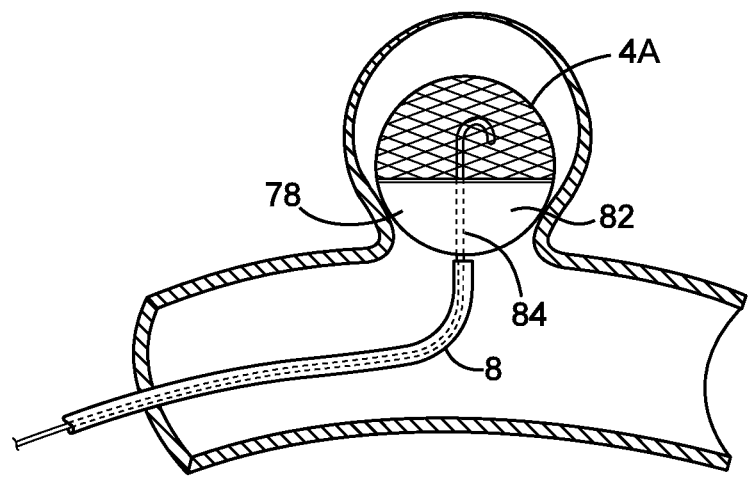
FIG. 18 shows the heating device used with the expandable device of FIGS. 11-14.
Figure 19:
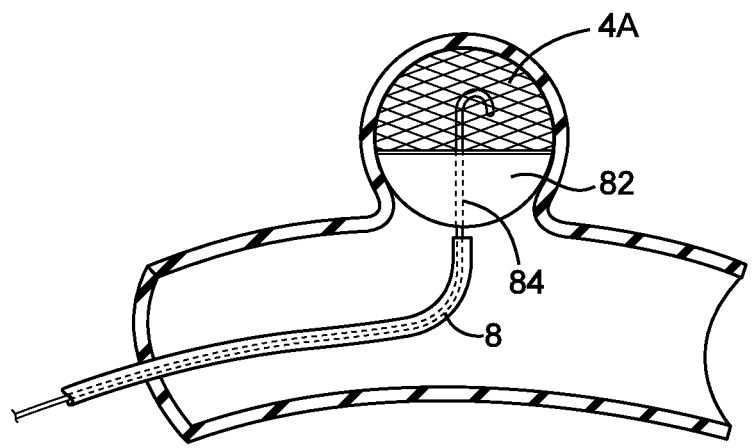
FIG. 19 shows the aneurysm shrunk into contact with the expandable device.
Figure 20:
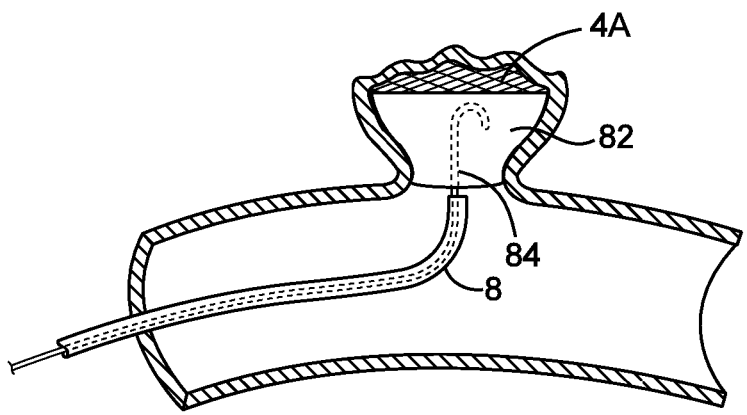
FIG. 20 shows the expandable device reduced in size during shrinking of the aneurysm.

Referring to FIGS. 18 and 19, the aneurysm may be shrunk into contact with the expandable device so that the expandable device 4A reinforces the aneurysmal wall to prevent rupture. The aneurysmal wall may also be shrunk further so that the expandable device 4A itself shrinks as shown in FIG. 20. After the aneurysm has been reduced in size, the sealant 64 may also be delivered to further seal the aneurysm.

Referring to FIGS. 1 and 21-24, another delivery catheter 110 for treating an aneurysm with the system 2 of FIG. 1 is shown. The catheter 110 is advanced to the carotid artery and the second catheter 8 is advanced through the first catheter 6 to the aneurysm. The delivery catheter 110 extends through the second catheter 8 to deliver an expandable device 4B to the aneurysm. The delivery catheter 110 has a lumen 112 which may be coupled to one or more of the various sources 18, 20, 22, 24. The expandable device 4B is coupled to the energy source 12 for heating and shrinking the aneurysm as will be described below.

Figure 21:
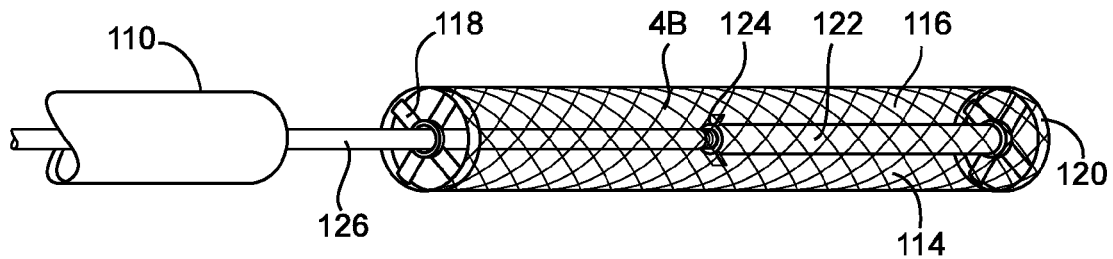
FIG. 21 shows another expandable device having a locking mechanism for holding the device in the expanded position.
Figure 22:
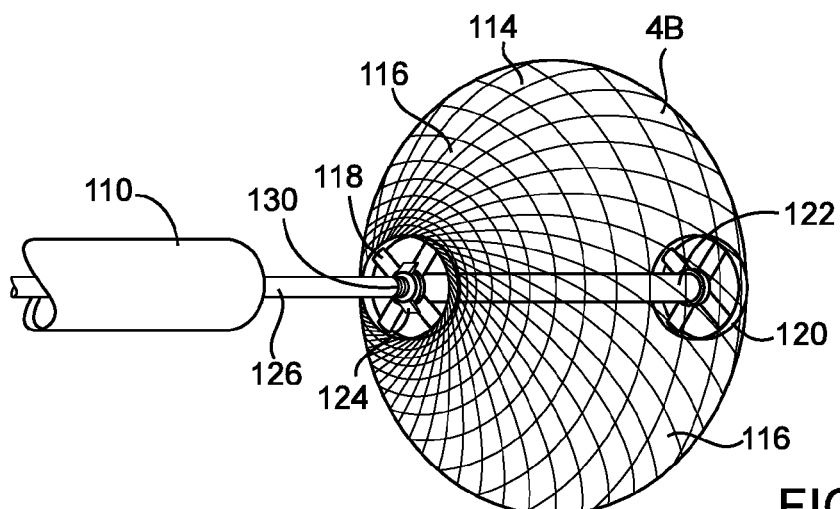
FIG. 22 shows the expandable device of FIG. 21 with the device in the expanded position.
Figure 23:
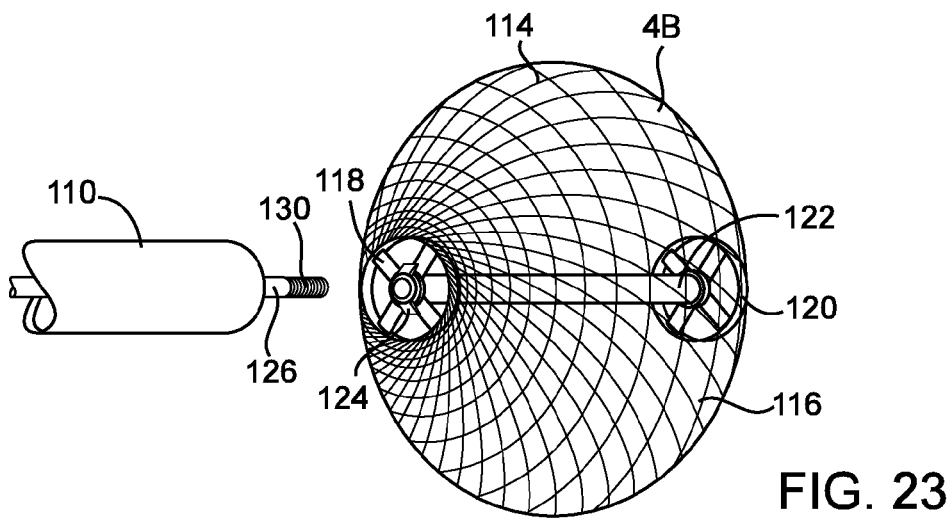
FIG. 23 shows the device of FIGS. 21 and 22 released from the delivery catheter.
Figure 26:
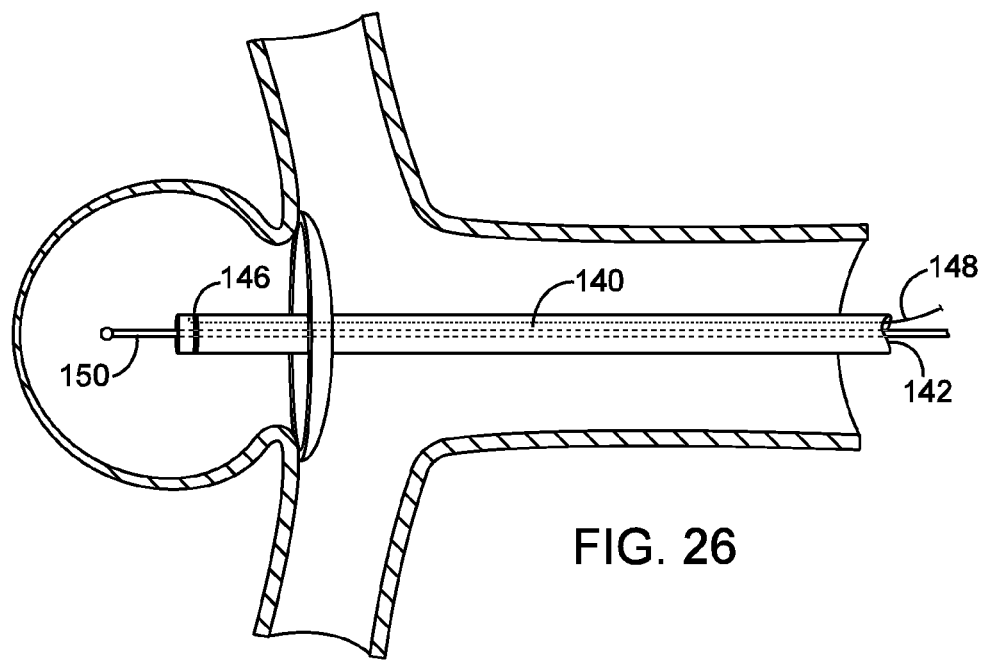
FIG. 26 shows the catheter of FIG. 21 with the cover having a curved shape.

The expandable device 4B is movable from the collapsed position of FIG. 21 to the expanded position of FIG. 22. Flexible filaments 114 preferably form a woven or braided mesh structure 116 extending between first and second hubs 118, 120. A central post 122 extends from the second hub 120 and has a locking mechanism 124 which engages the first hub 118 to hold the expandable device 4B in the locked position. An actuator 126, which is preferably a tapered rod 128, has a threaded connection 130 with the central post 122. The actuator 126 is pulled to move the locking mechanism 124 into engagement with the second hub 120. The locking mechanism 124 has spring elements 126 which are naturally biased to the position of FIG. 23. The spring elements 126 are angled proximally so that they are displaced inwardly by the hub 118 when the post 122 and spring elements 126 pass through the hub 118. After the spring elements 126 have passed through the hub 118 they assume their unbiased shape thereby locking the device 4B in the expanded position. The locking mechanism 124 may be any suitable locking mechanism.

The flexible filaments 114 preferably bias the device 4B toward the collapsed position so that the operator may partially expand the device to determine whether the device has the appropriate size. If the device is not the appropriate size, the device can be collapsed and withdrawn through the second catheter 8. After the expandable device 4B has been expanded, the aneurysmal wall may then be shrunk in any manner described herein. In the preferred embodiment of FIG. 21, the expandable device is a monopolar RF electrode with the energy source being an RF generator coupled to the actuator 126. The expandable device 4B may be insulated along a proximal portion 116 to protect the neck, parental vessel and adjacent vessels as mentioned above. After the aneurysmal wall has been reduced in size, the sealant 64 (FIG. 8) may be introduced to isolate the aneurysm from the parental vessel.

Figure 10:
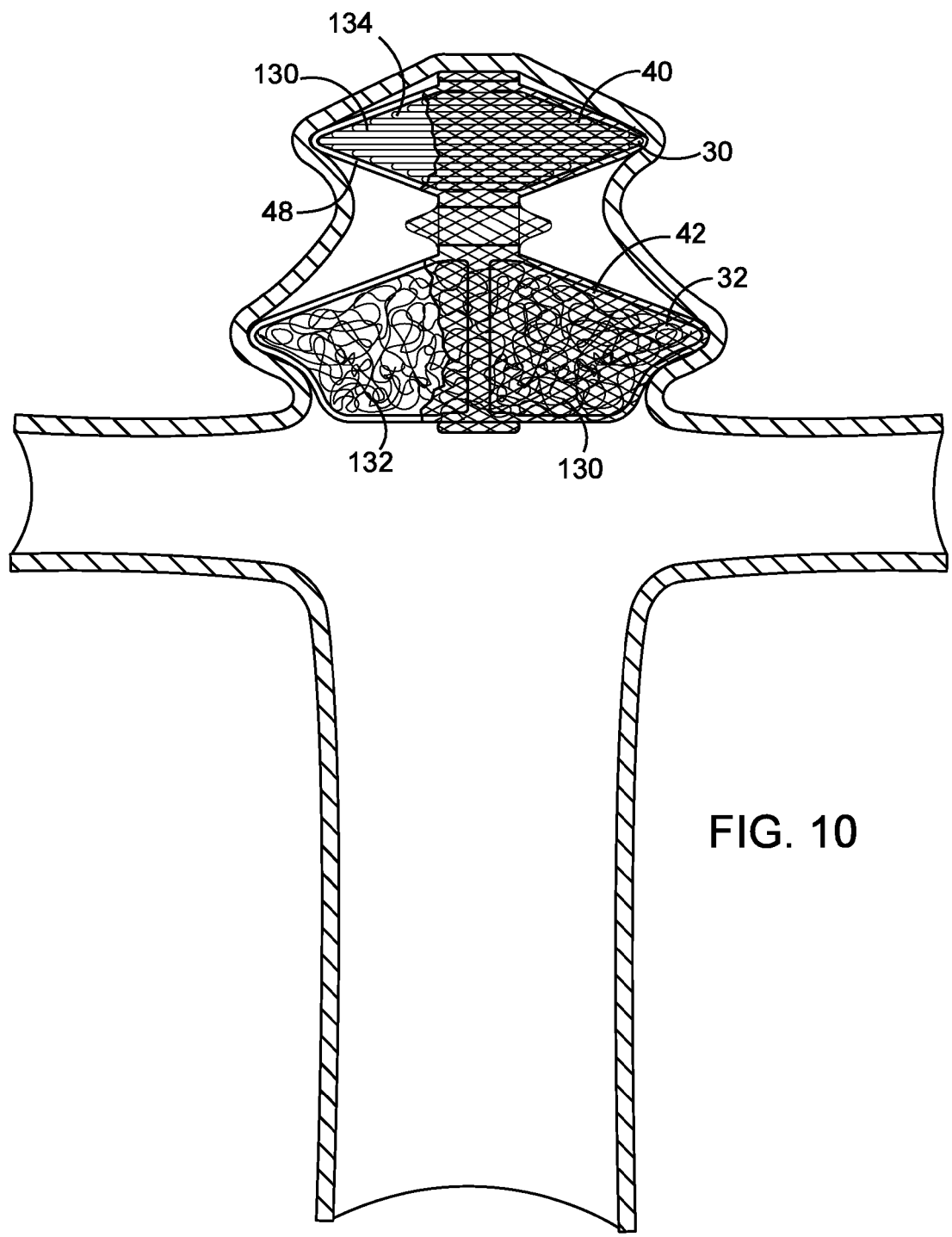
FIG. 10 shows the expandable device filled with an expandable material such as random fibers or a coil.
Figure 11:
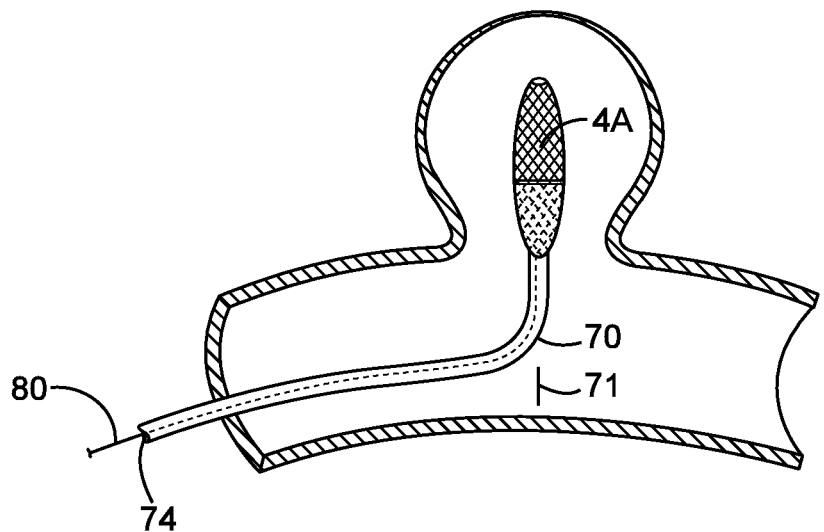
FIG. 11 shows another expandable device, which is deployed with a balloon in a collapsed position.

In another aspect of the present invention, the expandable devices 4, 4A, and 4B may be filled with an expandable thrombogenic material 130. Referring to FIG. 10, the expandable device 4 is filled with the compressible, thrombogenic material 130 which may be randomly oriented fibers 132 or coils 134. When the expandable device 4 is expanded, the material 130 expands to occupy the interior volume of the woven or braided mesh structure 42. The material 130 may be used with any of the expandable devices described herein without departing from the scope of the invention. When the material 130 includes filaments 136, the filaments 136 may be helically, radially or randomly oriented within the interior volume of the mesh or braided structure 42.

Referring to FIGS. 1 and 24-27, another catheter 140 for treating an aneurysm with the system of FIG. 1 is shown. The first catheter 6 is introduced through the femoral artery and advanced to the carotid artery. The second catheter 8 is advanced through the first catheter 6 to the aneurysm. The delivery catheter 140 is passed through the second catheter 8 to the aneurysm to treat the aneurysm.

Figure 27:
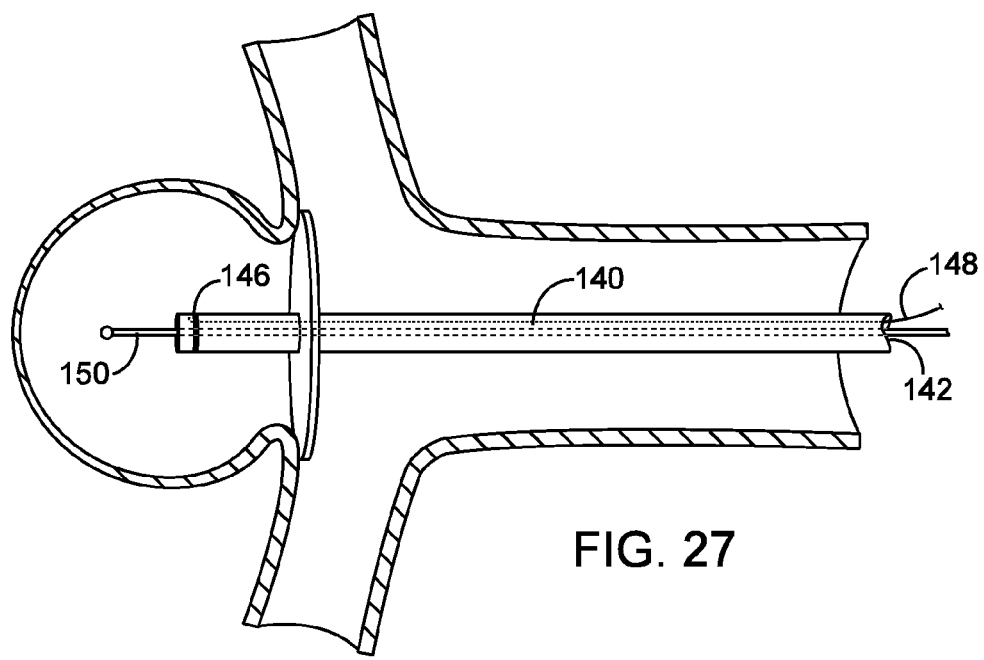
FIG. 27 shows the catheter of FIG. 21 isolating an aneurysm.

The delivery catheter 140 has a lumen 142 which is coupled to the sources of fluid, contrast, sealant and vacuum 18, 20, 22, 24. The distal end of the catheter 140 has a cover 144 which is positioned over the neck of the aneurysm as shown in FIG. 27. The cover 144 provides temporary isolation of the aneurysm from the parental vessel. The cover 144 is preferably a disc of relatively soft material such as silicone. The cover 144 is preferably configured to cover an area of about 0.8 mm$^2$ to 75 mm$^2$ and is relatively thin so that the cover 144 does not impede flow through the parental vessel and so that the cover 144 can distort to a small profile when passing through the second catheter 8. The cover 144 is also preferably impermeable so that the cover 144 can isolate the aneurysm from the parental vessel.

The catheter 140 has an electrode 146 which is coupled to the energy source 12 with a wire 148 extending through the catheter 140. The electrode 146 may be configured as a monopolar RF electrode for delivery of RF energy with a second electrode (not shown) in contact with the patient's skin. Alternatively, a second electrode 150 may be passed through the lumen 142 to provide monopolar or bipolar RF with the first and/or second electrodes 146, 150. Shrinking of the aneurysm may, of course, be accomplished with any of the methods described above. For example, the heating device 84 (FIG. 16) may be advanced through the lumen 142 to heat and shrink the aneurysm.

Figure 28:
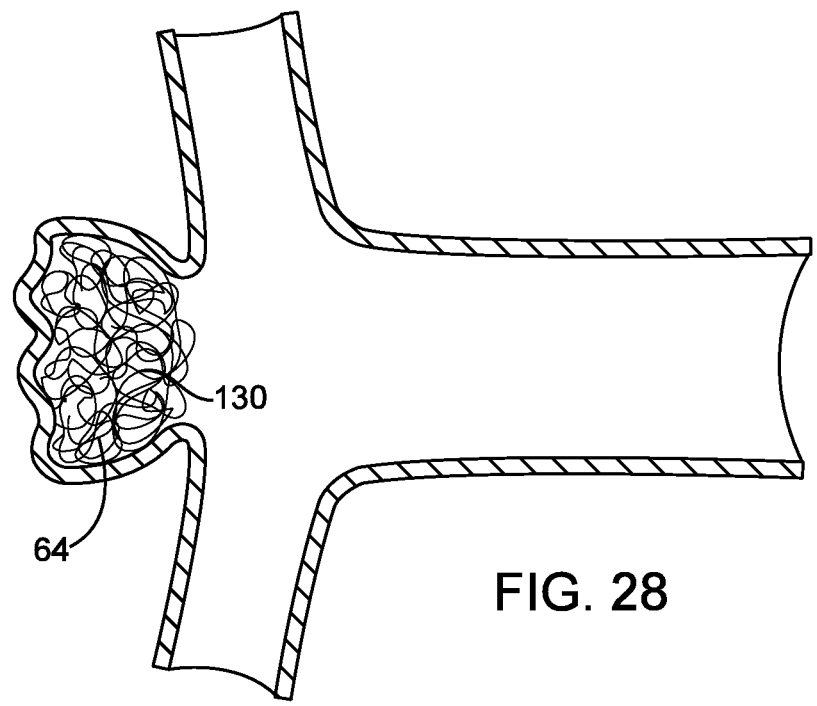
FIG. 28 shows the aneurysm reduced in size and a thrombogenic material and sealant introduced into the aneurysm.
Figure 29:
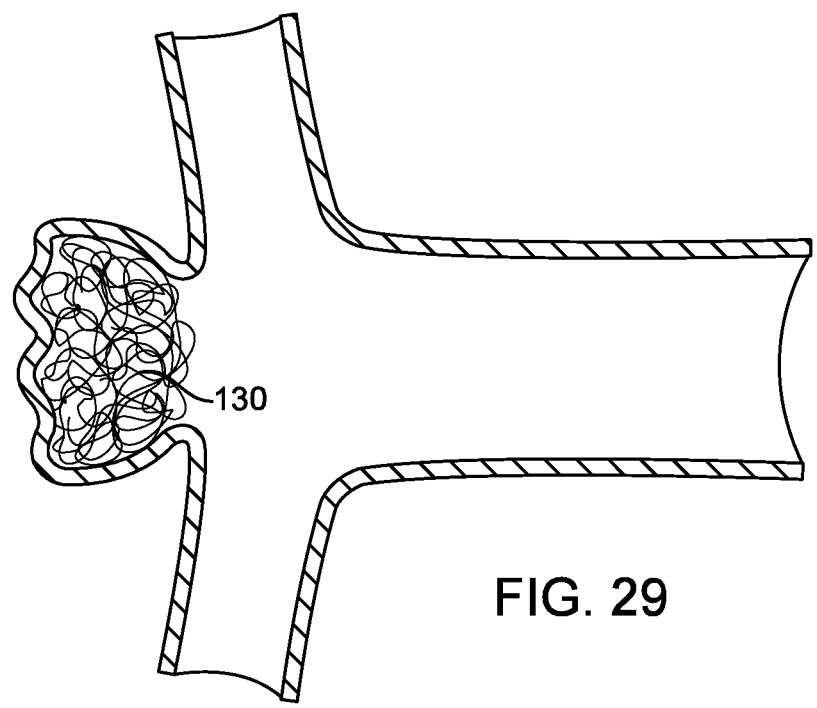
FIG. 29 shows only the thrombogenic material in the aneurysm.
Figure 30:
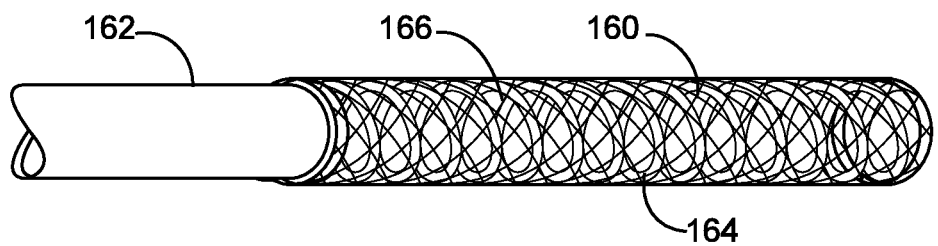
FIG. 30 shows another expandable device in a collapsed position.
Figure 31:
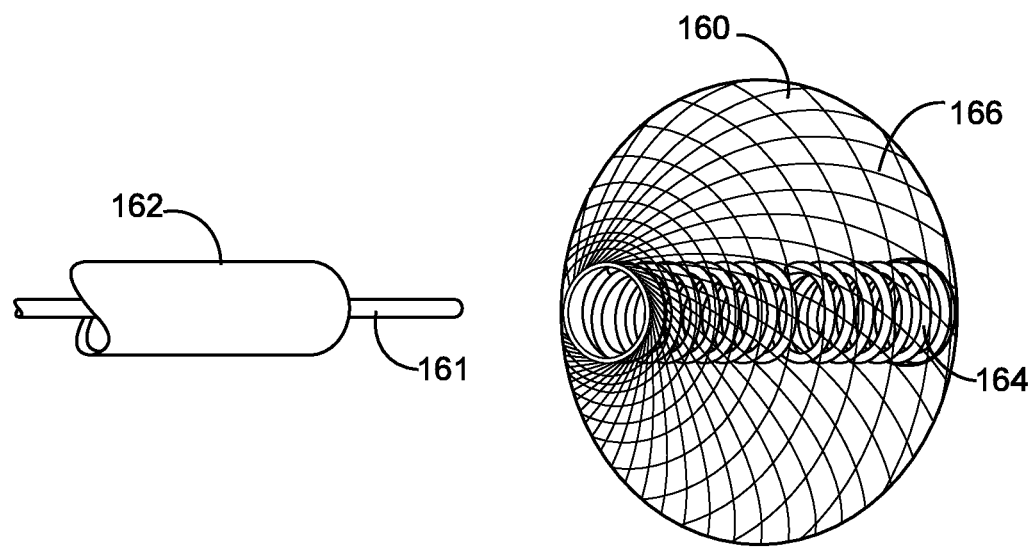
FIG. 31 shows the expandable device of FIG. 30 in an expanded position.

Use of the delivery catheter 140 is now described, the delivery catheter 140 is advanced through the second catheter 8 to the aneurysm. The cover 144 is positioned over the neck of the aneurysm and the aneurysm is heated to shrink the aneurysm. When using RF heating, fluid such as hypertonic saline may be infused into the aneurysm through the catheter 140 or second catheter 8 (FIG. 1). The cover 144 may be flexible enough to deflect and permit hot fluid to be slowly expelled into the parental vessel. Alternatively, the cover 144 may be periodically moved away from the neck so that hot fluid in the aneurysm may be slowly expelled into the parental vessel. The aneurysm may be reduced to an acceptable size or partially shrunk and filled with the thrombogenic material 130 and sealant (FIG. 28) or just the material 130 (FIG. 29). Although the delivery catheter 140, and particularly the cover 144, have been described in connection with RF delivery, the cover 144 may be incorporated into any of the other catheters described herein or any other catheter without departing from the scope of the invention.

Figure 32:
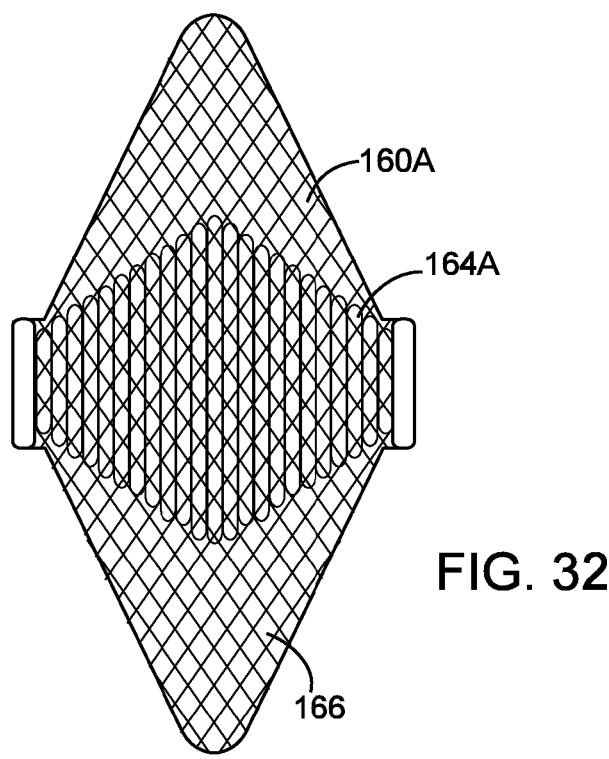
FIG. 32 is an alternative embodiment of the device of FIGS. 30 and 31.
Figure 33:
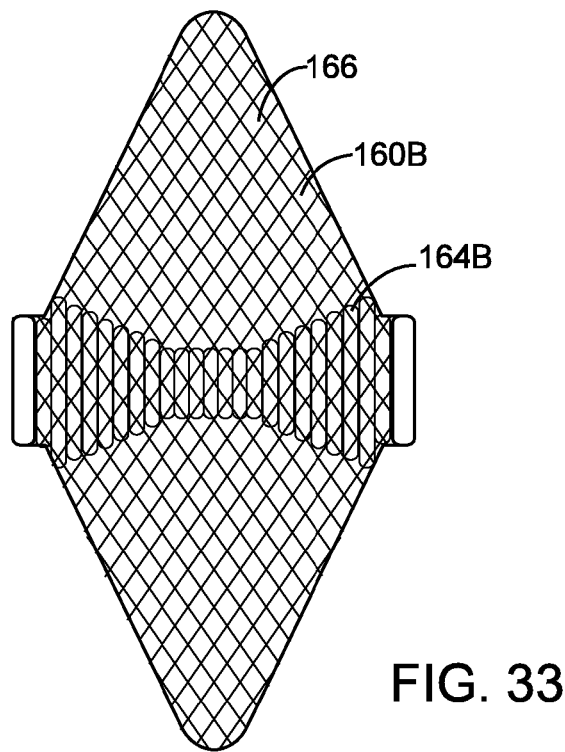
FIG. 33 is another alternative embodiment of the device of FIGS. 30 and 31.

Referring to FIGS. 30-34, another expandable device 160 is shown for use with the system of FIG. 1. The expandable device 160 is advanced through the second catheter 8 with a delivery catheter 162. The expandable device has a mesh 166 which covers a spring 160 made of a shape memory material. The expandable device 160 is in the collapsed shape of FIG. 30 when advanced through the second catheter 8. After the expandable device 160 is within the aneurysm, a wire 161 or other device can be advanced to contact the device 160 to heat the device and the aneurysm. Upon heating, the coil collapses to the shape of FIG. 31 to move the mesh 166 to the expanded condition. Heating of the coil may be undertaken in any manner described herein. An advantage of the device 160 is that the device may be heated together with the aneurysm to deploy the device 160 while shrinking the aneurysm. Referring to FIG. 32, another device 160A is shown which is substantially the same as the device 160 except that spring 160A expands in the middle. FIG. 33 shows still another device 160B which has a smaller diameter in the middle to impede fluid flow through the spring 160.

Figure 34:
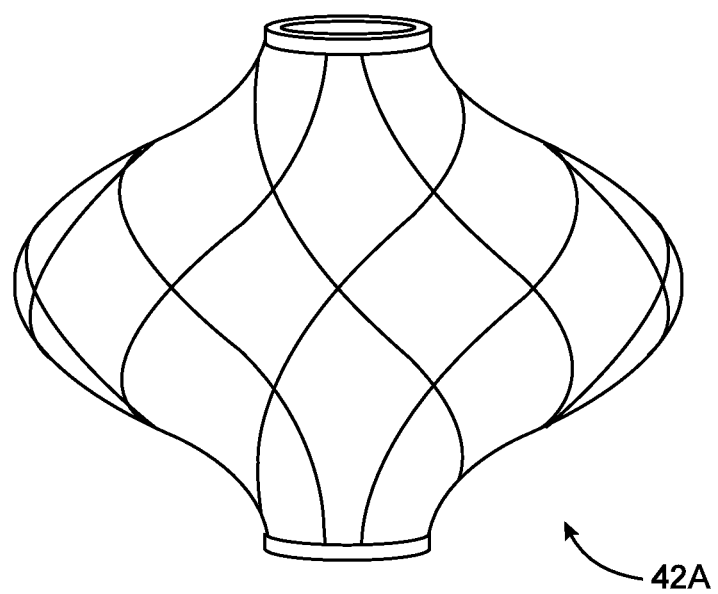
FIG. 34 shows a mesh structure for use with any of the expandable devices described herein.

Referring to FIG. 34, another mesh 42A is shown. The mesh 42A may be used with any of the expandable devices described herein and the mechanism for expanding and holding the mesh 42A has been omitted from FIG. 34 for clarity. Any of the actuating and delivery methods and devices described above or any other suitable device may be used with the mesh 42A. The mesh 42A preferably has 10-50 filaments, more preferably 20-50 filaments, extending between first and second ends 150, 152. The filaments 148 are preferably platinum alloy (such as 92% platinum, 8% tungsten). The filaments 148 preferably form a tube in the collapsed position which has a diameter of no more than 0.020 inch but expands to a diameter of at least 0.200 inch at a central portion 154.

Figure 35:
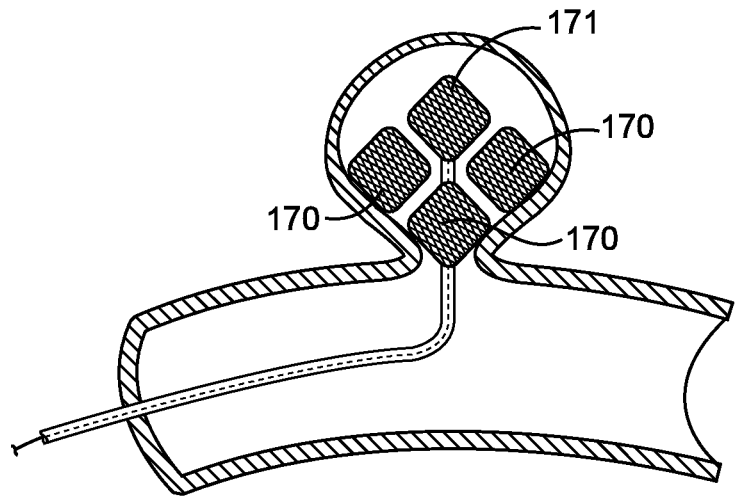
FIG. 35 shows a number of expandable device delivered to the aneurysm.
Figure 36:
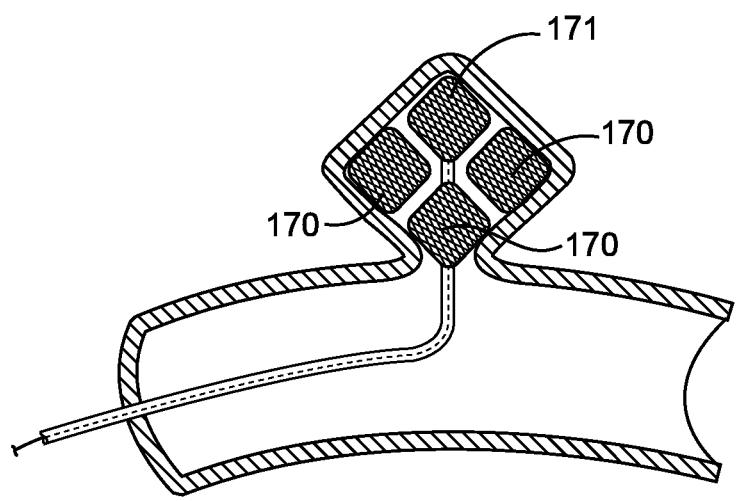
FIG. 36 shows the aneurysm of FIG. 35 reduced in size.

The devices described herein are preferably delivered to the aneurysm to occupy the remaining volume of the aneurysm after shrinking the aneurysm. Referring to FIGS. 35 and 36, a number of devices 170 may be delivered to the aneurysm with one of the devices 171 being used to heat and shrink the aneurysm. The devices 170 may be partially or completely insulated in the manner described above to protect the neck while heating and shrinking is accomplished with the device 171. The devices 170 and 171 are shown spaced apart for clarity but, of course, will be closely packed together when filling the aneurysm. The devices 170 and 171 may be any of the expandable devices described herein or any other suitable device without departing from the scope of the invention.

Figure 37:
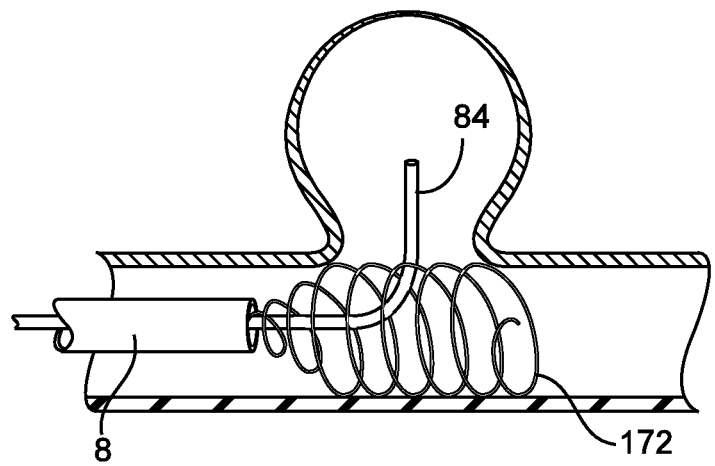
FIG. 37 shows a coil for regulating flow between an aneurysm and a parent vessel.
Figure 38:
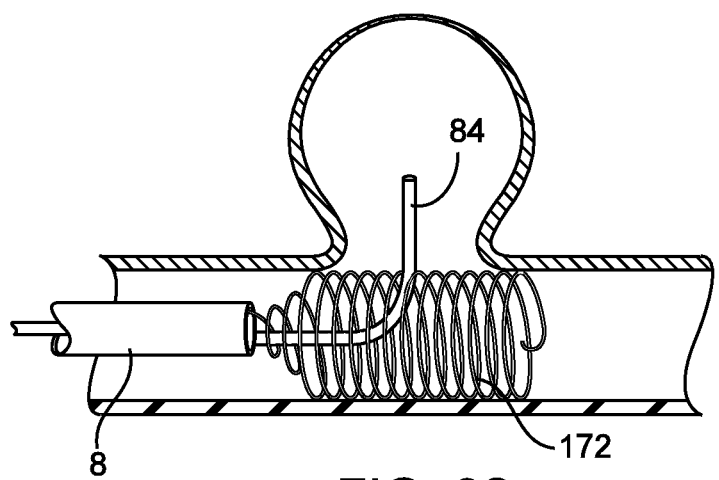
FIG. 38 shows the coil of FIG. 37 with the windings spaced close together to further impede fluid flow between the aneurysm and the parent vessel.

Referring to FIG. 37, another system for reducing the size of an aneurysm is shown. A coil 172 is used to regulate flow of fluid between the aneurysm and the parent vessel. The coil 172 is particularly useful for holding heated fluid in the aneurysm to heat and shrink the aneurysm. The heating device 84 of FIGS. 16 and 17, or any other suitable device for heating the aneurysm, is introduced into the aneurysm to heat and shrink the aneurysm. The coil 172 is manipulated by pulling or pushing the coil to retract or deploy the coil 172 from the catheter 8 (see FIG. 1). The pitch of the coil 172 can be varied by pulling or pushing the catheter 8 relative to the coil 172. The windings of the coil 172 may be close together so that the coil 172 substantially impedes flow between the aneurysm and the parent vessel (FIG. 38) or may be spaced-apart to permit slow leakage of fluid into the parent vessel. The coil 172 may be made of any suitable material and is preferably a shape-memory alloy such as nitinol.

Figure 40:
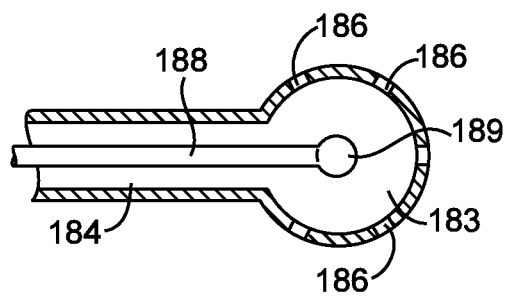
FIG. 40 is a cross-sectional view of the distal end of the catheter of FIG. 39.
Figure 39:
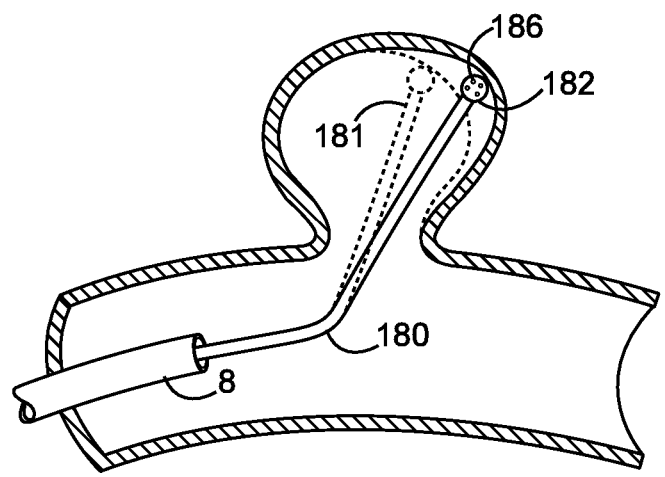
FIG. 39 shows another catheter for heating tissue.

Referring to FIGS. 39 and 40, another catheter 180 for heating and shrinking an aneurysm is shown. The catheter 180 is preferably less than 5 Fr, more preferably 2-4 Fr, and most preferably about 3 Fr in size so that it is small and flexible enough to shrink select portions of the aneurysm as shown by dotted lines 181 in FIG. 39. The catheter 180 may, of course, be sized larger to shrink larger portions of the aneurysm or other tissue structures. The catheter 180 has a tip 182 which is made of a heat-resistant, non-stick material (such as PTFE) so that the tip can contact the tissue during heating without sticking to the tissue. The catheter 180 may also be a hypotube, guidewire or similar device without departing from the scope of the invention. The tip 182 forms a chamber 183 and has holes 186 formed therein for delivery of a conductive fluid as described below.

Figures 41, 42:
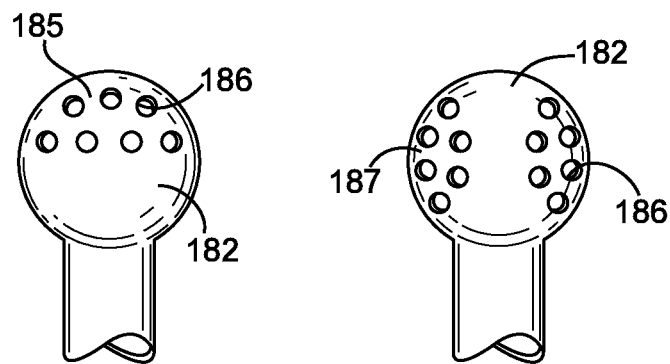
FIG. 41 shows the tip of the catheter of FIGS. 39 and 40 with holes at the distal end of the tip.
FIG. 42 shows the tip of the catheter of FIGS. 39 and 40 with holes along the side of the tip.
Figure 43:
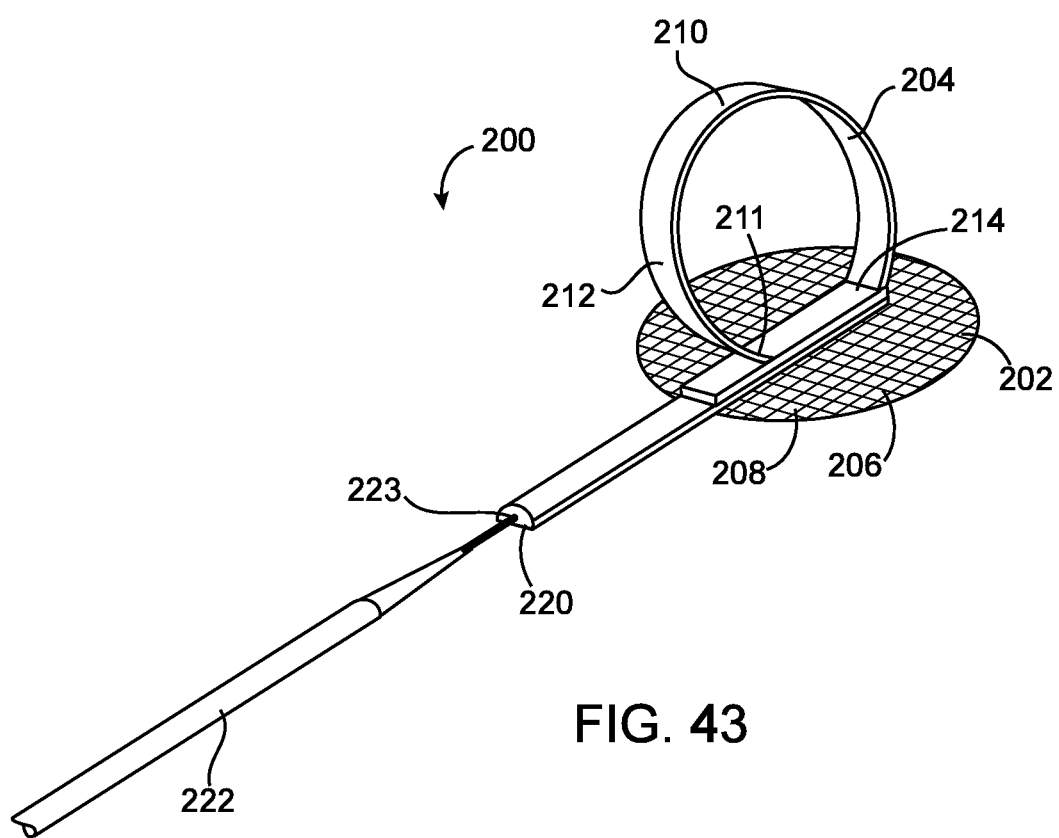
FIG. 43 shows another device for treating an aneurysm.

The catheter 180 has a lumen 184 which communicates with the chamber 183 in the tip 182. The lumen 184 is coupled to the source of fluid 18 (see FIG. 1) which is preferably hypertonic saline. An RF probe 188 passes through the lumen 184 and is coupled to the energy supply 12 (see FIG. 1) which is preferably an RF generator. The RF probe 188 has an electrode 189 positioned in the chamber while a second electrode (not shown) is positioned in contact with the patient's skin in the conventional manner. When the conductive fluid is delivered through the lumen 184, electrical energy is conducted by the conductive fluid to heat the aneurysm. The holes 183 in the tip 182 may be distributed around the tip 182 (FIGS. 39 and 41), positioned at the distal end 185 (FIG. 42) or along the sides 187 (FIG. 43) of the tip 182.

After the volume of the aneurysm has been reduced, the aneurysm may be treated in any other manner described herein. Furthermore, the catheter 180 of FIGS. 39-43 may be used to heat tissue or fluid in connection with any of the other embodiments described herein and in particular as a substitute for the device 84 of FIGS. 16 and 17. Finally, the catheter 180 may be used to heat tissue for any other suitable purpose including those described above. For example, the catheter 180 may be useful in treating venous insufficiency, deep vein reflux or for vein stripping. Furthermore, the catheter 180 may be useful for treating urinary incontinence.

Referring to FIG. 43-46, another device 200 for treating an aneurysm is shown. The device 200 has a cover 202 that covers the neck of the aneurysm. The device 200 also has a lateral extension 204 extending from the cover 202 into the aneurysm. The lateral extension 204 positions the cover 202 over the neck of the aneurysm and anchors the device 200 to the aneurysm.

The cover 202 may be any suitable structure such as a patch or tube so long as the cover 202 is able to block the neck of the aneurysm to isolate the aneurysm from the parental vessel. The cover 202 is preferably substantially flat so that the cover 202 can lie against the wall of the parental vessel around the neck of the aneurysm. In the preferred embodiment, the cover 202 is preferably a mesh patch 206 made of a superelastic material such as nitinol. The mesh 206 may have a coating or layer 208, such as expanded PTFE, which provides the properties and advantages of conventional graft materials. The cover 202 preferably extends no more than one half, and more preferably no more than one third, the circumference of the vessel. Stated another way, the cover 202 preferably extends no more than 180 degrees and more preferably no more than 120 degrees around a longitudinal axis of the device when expanded. Of course, the cover 202 may cover more or less of the parental vessel without departing from various aspects of the invention.

The lateral extension 204 preferably forms 1-8 loops 210, and more preferably only one loop, extending from the cover 202. The loop 210 is preferably formed by an elongate element 212 such as a ribbon made of a superelastic or shape-memory material such as nitinol. An end 211 of the loop 210 is attached to a guide 214 which is attached to the cover 202. The term loop 210 is intended to include any filament, ribbon, wire or the like having two sides coupled to the cover 202. The two sides do not have to touch or be adjacent one another to form a loop 210 and, in fact, the loop could be made from a continuous coil wrapped into the cover 202 so long as the coil generally forms 1-8 individual loops 210 extending into the aneurysm. The lateral extension 204 extends laterally from a catheter 216 during deployment so that the catheter 216 can remain aligned with the vessel in the manner shown in FIG. 45.

The elongate element 212 extends and slides through the guide 214. The element 212 has a stop 220 at one end that engages the guide 214 to hold the extension 204 in the expanded condition. The element 212 is preferably biased toward the expanded position of FIGS. 43 and 46 so that the stop 220 naturally engages the guide 214 when the element 212 is released. The element 212 is coupled to a first manipulator 222 with a releasable connection such as a threaded connection 223 or an electrolytically severable bond. The first manipulator 222 is used to move and deploy the device 200, and in particular the loop 210, in the manner described below. As will be explained below, the device 200 is preferably available in a number of different sizes with the size of the loop 210 and the size of the cover 202 being variable. The size of the loop 210 and cover 202 are selected based upon the geometry of the aneurysm and parental vessel.

Figure 44:
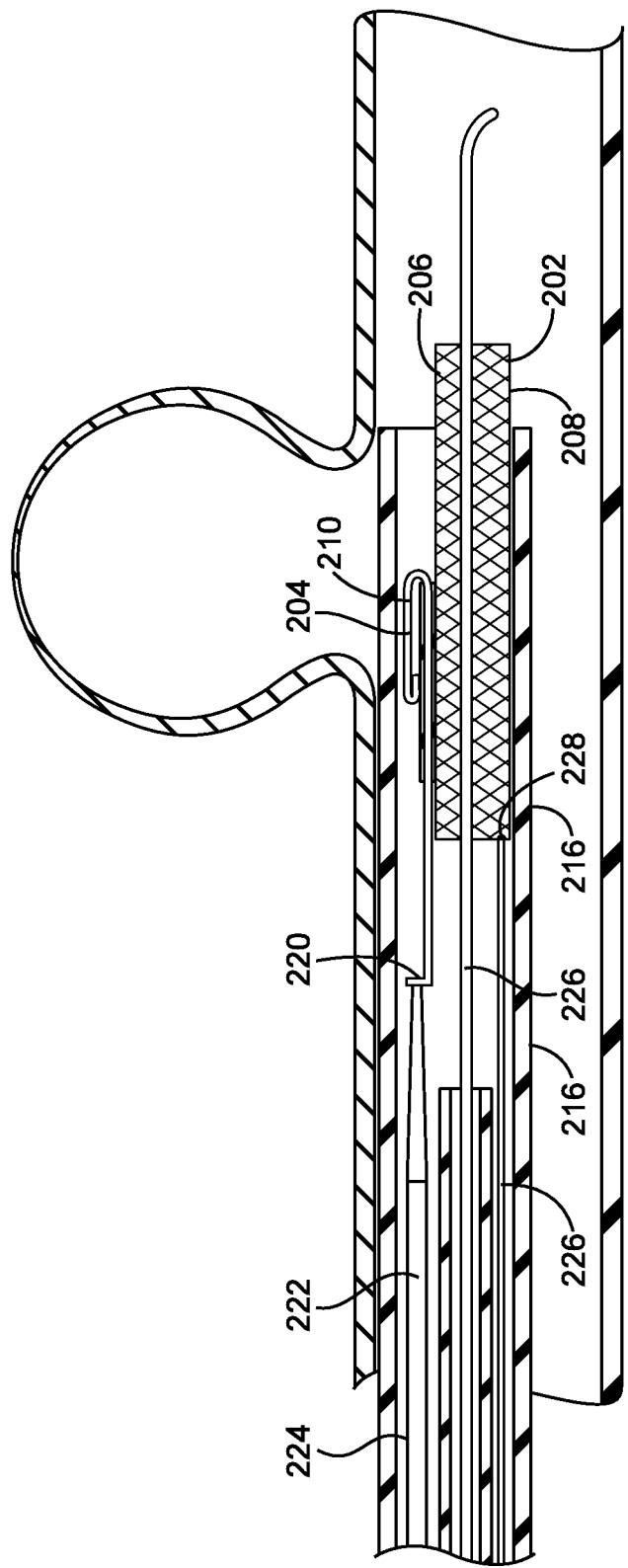
FIG. 44 shows the device of FIG. 43 contained within a catheter for delivery to the aneurysm.
Figure 45:
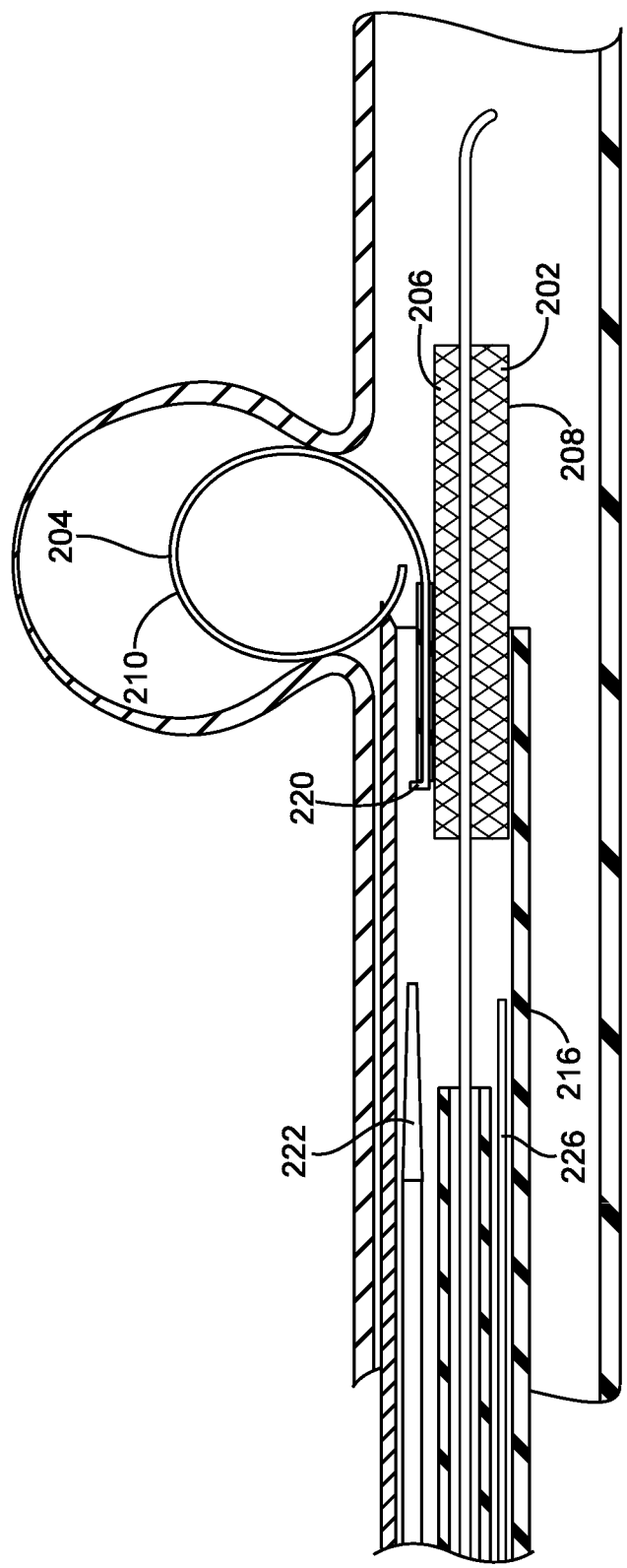
FIG. 45 shows an extension of the device positioned in the aneurysm.
Figure 46:
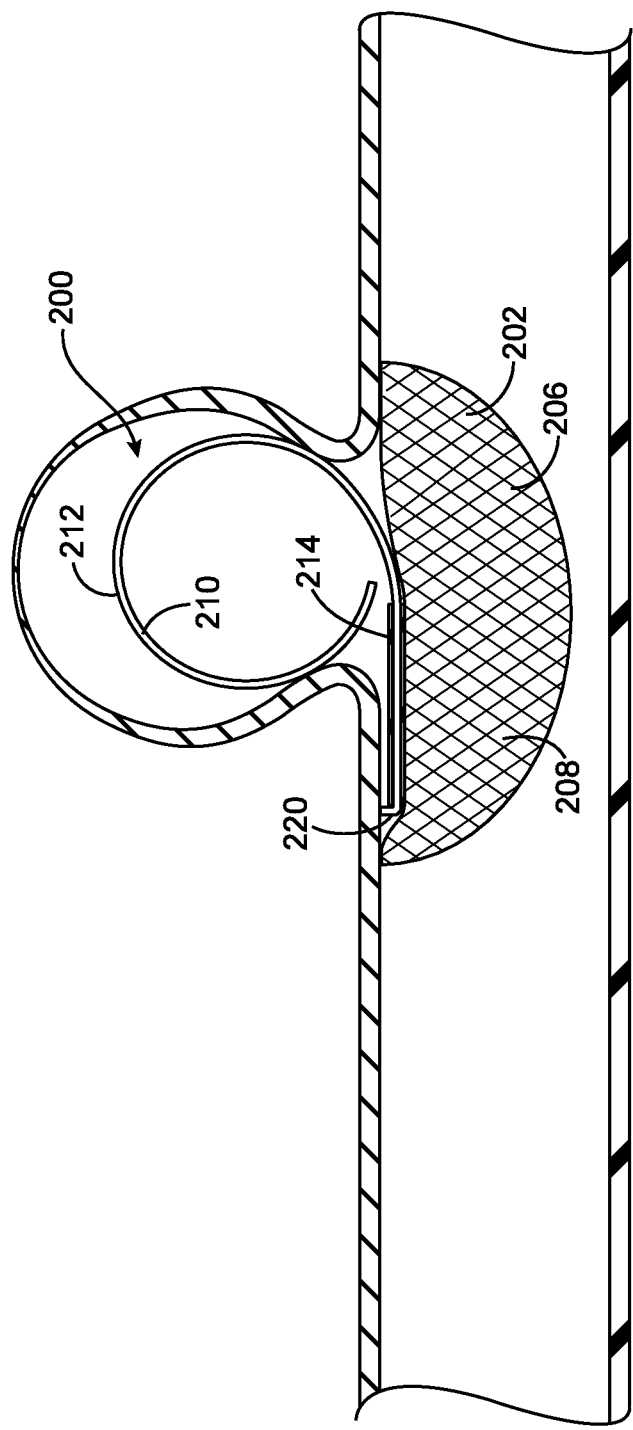
FIG. 46 shows the device of FIGS. 43-45 deployed with a cover over the neck of the aneurysm.
Figure 47:
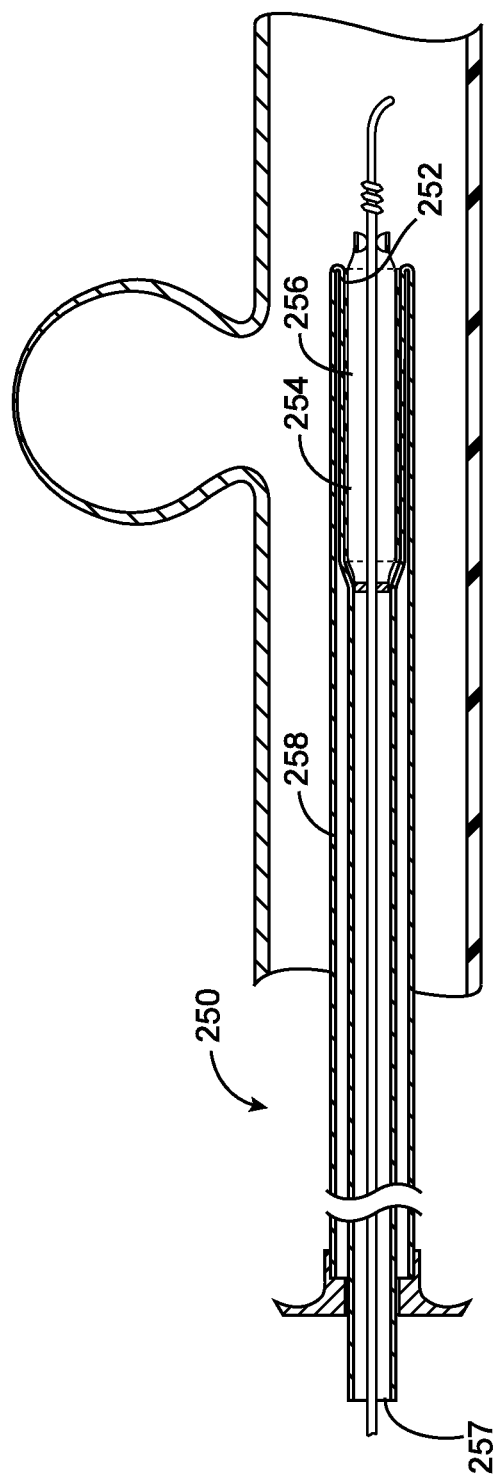
FIG. 47 shows another device for treating an aneurysm.
Figure 48:
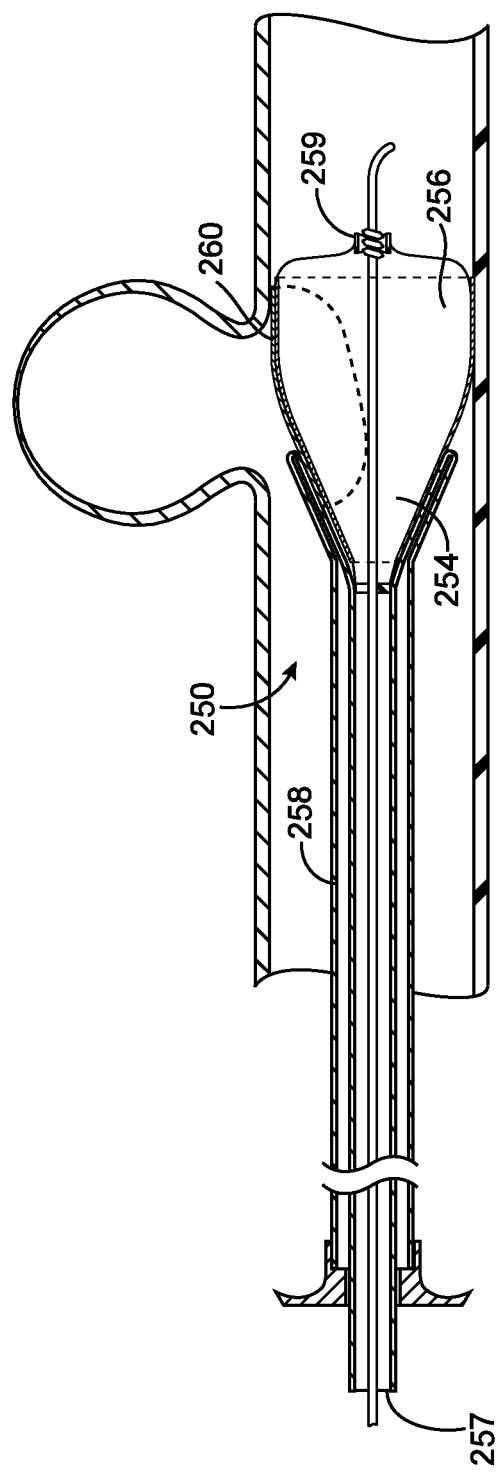
FIG. 48 shows the device of FIG. 47 partially deployed with an expandable element.
Figure 49:
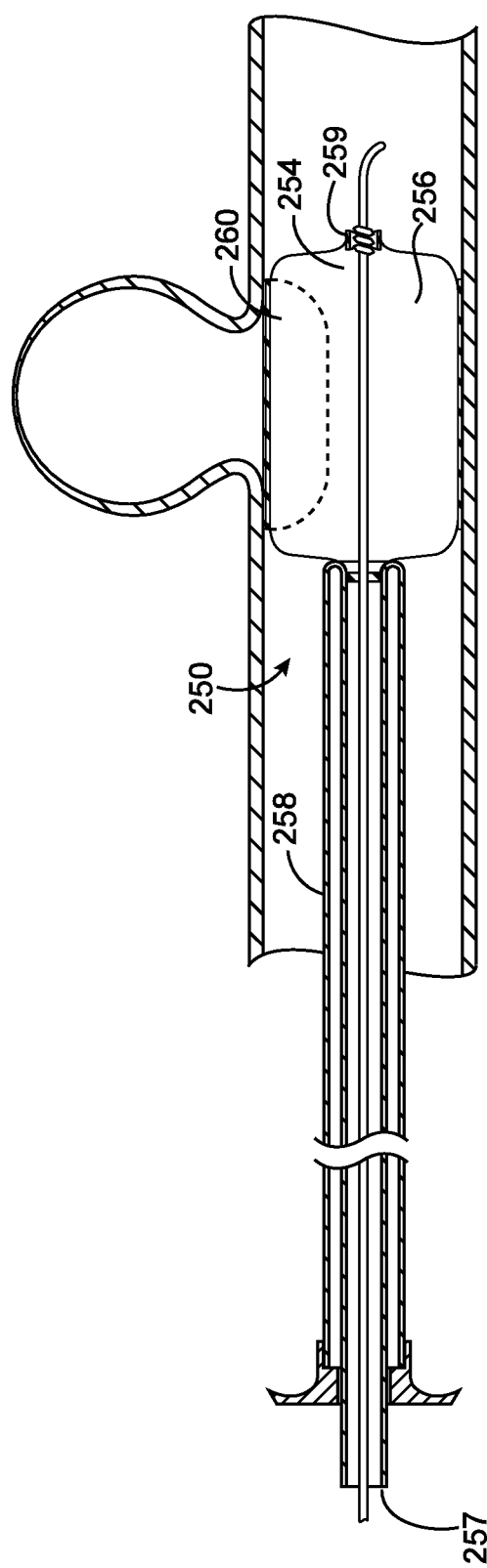
FIG. 49 shows the device of FIG. 48 with the sheath full retracted and the expandable element expanded to move the cover over the neck of the aneurysm.

The device 200 is preferably delivered with the catheter 216. The device 200 is mounted within the catheter 216 and is advanced out of the catheter 216 and exposed as shown in FIGS. 44-46 when deploying the device 200. The delivery catheter 200 has a first lumen 224 in which is positioned the first manipulator 222. A second manipulator 226 holds the cover 202 opposite the first manipulator 222 for moving and deploying the device 200. A suture 228 or any other releasable connection holds the cover 202 to the second manipulator 226. The catheter 216 is preferably advanced over a guidewire 230 which is positioned in a guidewire lumen 232. The catheter 216 preferably has a three-lumen configuration although fewer lumens may be used without departing from the scope of the invention.

The device 200 may also be operated by delivering energy, such as RF energy, to the device 200 as now described in connection with methods and systems of the invention. When delivering energy, such as RF energy, the cover 202 preferably does not conduct energy to protect the parental vessel and neck of the aneurysm.

Additional methods of the present invention are now described in connection with the preferred embodiment of FIGS. 43-46 although other suitable devices may be used. Before introducing the device 200 into the patient, the geometry of the aneurysm and parental vessel are determined so that the appropriate size of the device 200 is used. For example, the size of the extension 204 may be selected to be somewhat smaller than the aneurysm particularly when heat is used to shrink the aneurysm with RF energy or the like. The device 200 may also form a number of different shapes that are selected based on the geometry of the aneurysm.

After selecting the appropriate size of the device 200, the device 200 is introduced into the patient with the catheter 216 in the manner described above and the methods and systems described above are specifically incorporated here. When the device 200 is positioned at the aneurysm, the distal end of the cover 202 and the lateral extension 204 are advanced out of the catheter 216 by manipulating the first and second manipulators 222, 226. The first and second manipulators 222, 226 may be used to expand and retract the device 200 a number of times when attempting to introduce the extension into the aneurysm. Once the extension 204 is properly positioned within the aneurysm, the extension 204 expands to occupy space within the aneurysm.

Energy may then be delivered to the lateral extension 204 to shrink the aneurysm and/or simply adhere the extension to the aneurysmal wall thereby holding the cover in the proper position. The source of RF energy is coupled to the first manipulator 222 for this purpose. Although the invention may be practiced with delivery of RF energy, various aspects may be practiced without delivering energy to the aneurysm. The device 200 is then released to permit the cover 202 to expand as shown in FIG. 46. The lateral extension 204 helps to orient the cover 202 into the proper position as the cover 202 expands.

Referring to FIGS. 47-50, still another device 250 for treating an aneurysm is shown. The device 250 has a cover 252 wrapped around an expandable element 254 such as an inflatable balloon 256. The balloon 256 is inflated through an inflation lumen 257. A sheath 258 extends over the cover 252 to trap the cover 252 between the sheath 258 and expandable element 254. The sheath 258 is retracted to expose the cover 252 when deploying the cover 252 as explained below. The sheath 258 is preferably folded over itself at the distal end and is folded back and everted to expose the cover 252. The sheath 258 is preferably made of a flexible material at the distal end such as a suitable polymer such as polyethylene. The guidewire may engage the expandable element 254 at a connection 259 so that the guidewire helps to stabilize the device 250 during deployment.

The cover 252 is preferably wrapped or collapsed by simply wrapping the cover 252 around the expandable element 254. The cover 252 may overlap itself or may extend around only part of the expandable element 254. In the preferred embodiment, the cover 252 is wrapped around the expandable element 254 without any overlapping flaps, folds or sections.

The cover 252 is preferably adhered to the wall of the parental vessel around the neck of the aneurysm. The cover 252 may be adhered to the wall with any suitable method including glue or heat. The cover 252 may also be adhered to the wall using a conventional stent or with a support structure similar to a stent. In a preferred method, the cover 252 is adhered to the parental vessel with a biocompatible adhesive 260 such as cyanoacrylate applied to an outer surface of the cover 252. The sheath 258 covers the adhesive 260 during introduction and advancement of the device 250. The adhesive 260 may also be activated within the patient using light, heat, RF, radiation, chemical or other suitable activators.

Figure 51:
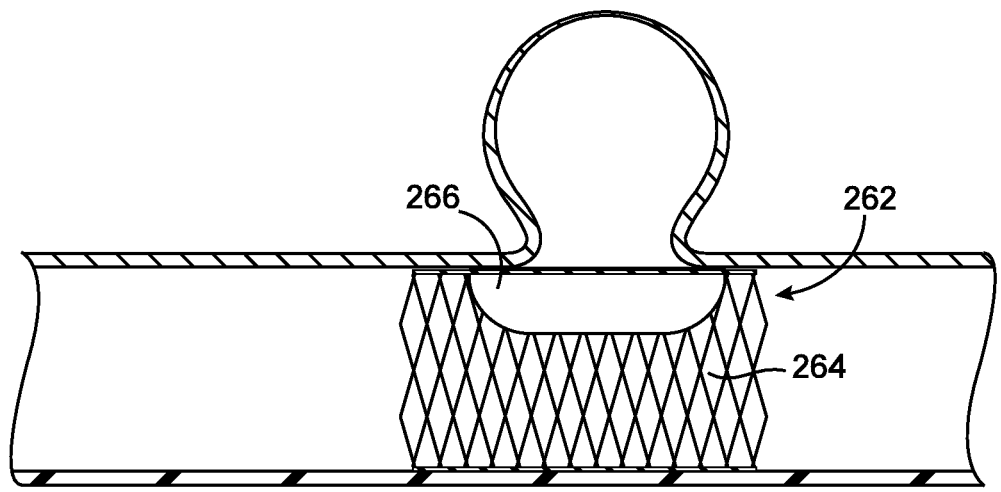
FIG. 51 shows an alternative cover for the device of FIGS. 47-49.
Figure 50:
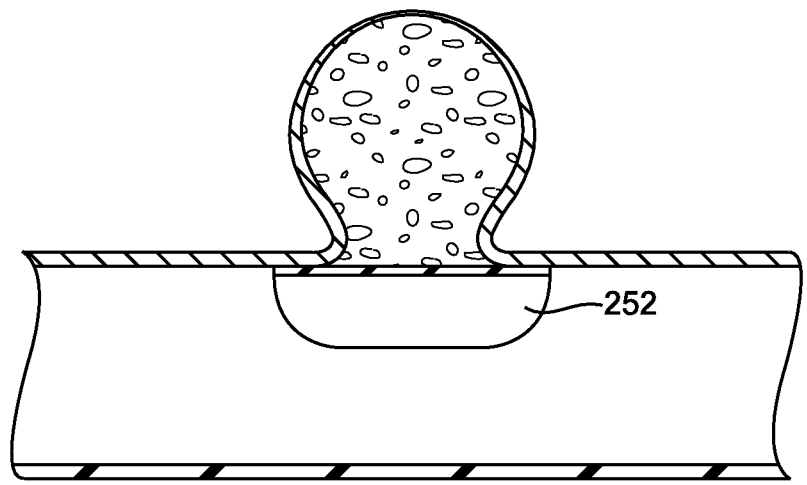
FIG. 50 shows the device of FIG. 47-49 fully deployed.
Figure 52:
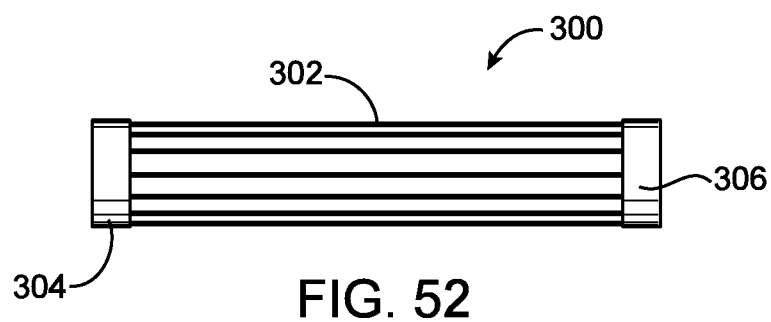
FIG. 52 shows yet another device for treating aneurysms in a collapsed position.
Figure 53:
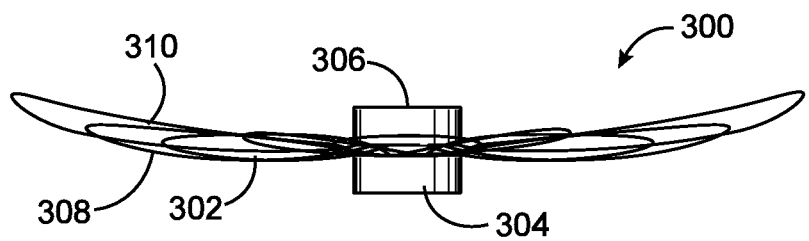
FIG. 53 is a side view of the device of FIG. 52 in an expanded condition.
Figure 54:
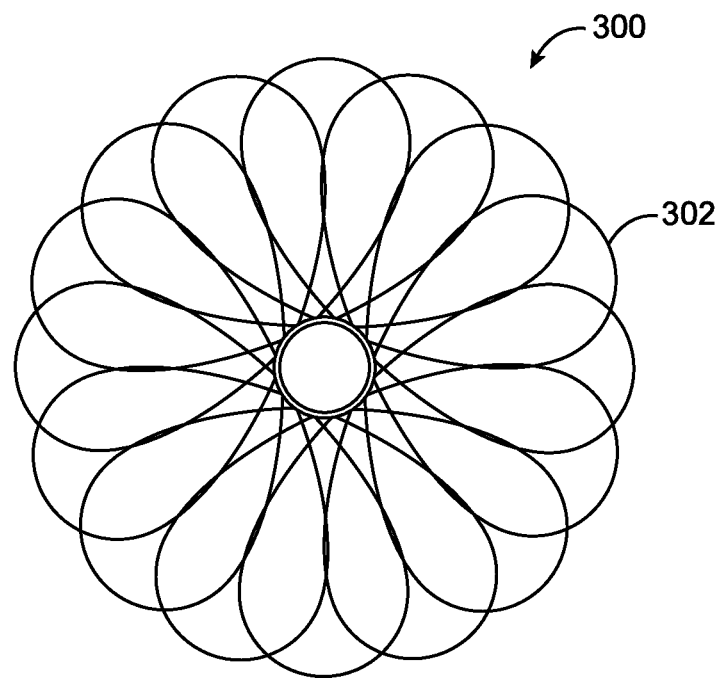
FIG. 54 is a plan view of the device of FIG. 52 in an expanded condition.
Figure 55:
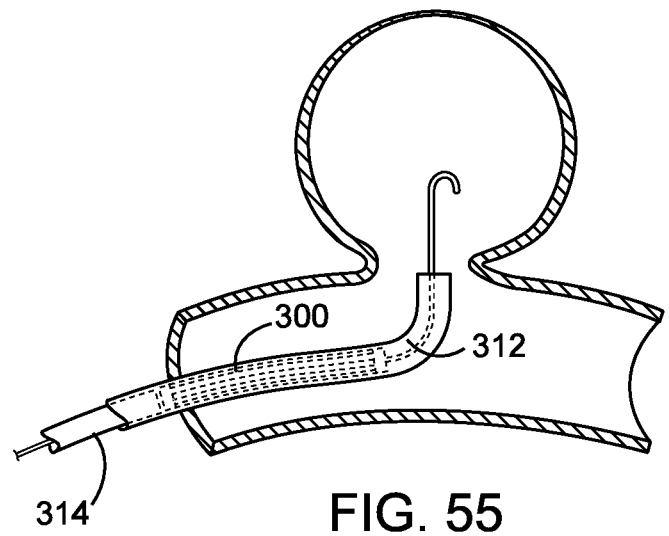
FIG. 55 shows a catheter delivering the device of FIGS. 52-54 to an aneurysm.
Figure 56:
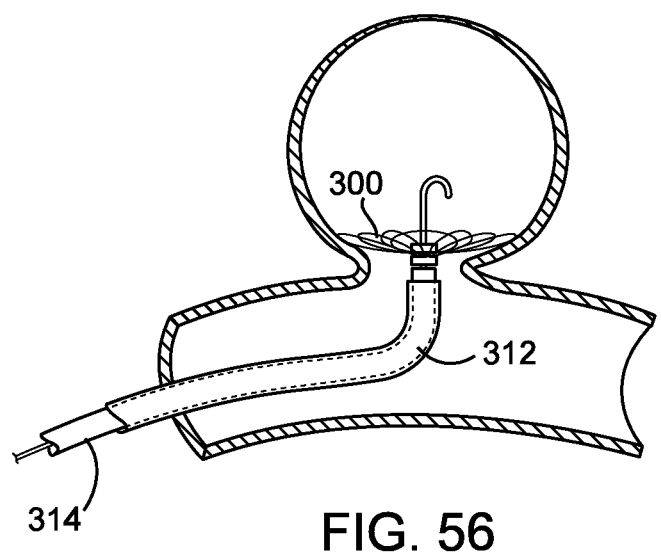
FIG. 56 shows the device of FIGS. 52-54 deployed in the aneurysm.
Figure 57:
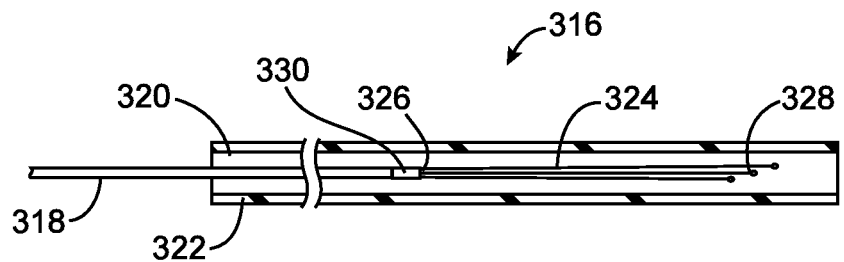
FIG. 57 shows still another device for treating an aneurysm.

Referring to FIG. 51, another cover 262 is shown for use with the device 250 wherein the same or similar reference numbers refer to the same or similar structure. The cover 262 has a frame 264, preferably metallic, and an impermeable portion 266 mounted to the frame 264. The impermeable portion 266 is preferably PTFE or expanded PTFE and is fused or sutured to the frame 264. The impermeable portion 266 covers the neck of the aneurysm to isolate the aneurysm.

Referring to FIG. 52-56, another device 300 for treating an aneurysm is shown. The device 300 has a number of filaments 302 that extend from a proximal hub 304 to a distal hub 306. The filaments 302 are preferably stainless steel, platinum or nitinol and the hubs 304, 306 are preferably platinum or a radiopaque polymer. The filaments 302 are attached to the hubs 304, 306 by solder, weld or glue. The device 300 preferably includes 2-16 filaments 302 and more preferably about 8 filaments 302. The filaments 302 may be integrally formed with one or both of the hubs 304, 306 or may be a single filament 302 which is wound around or adhered to the hubs 304, 306. The device 300 preferably assumes a generally dish-shaped structure having a generally convex side 308 and a concave side 310 although the device 300 may take any other suitable shape.

The device 300 is advanced through a catheter 312 with a manipulator 314. The device 300 may, of course, be mounted within a sheath (not shown) which is then advanced through the catheter 312 as described above. The manipulator 314 may simply push the device 300 or the device may be releasably attached to the device 300 with a mechanical connection or an electrolytically severable bond. When the device 300 exits the catheter 312, the distal hub 306 is naturally biased toward the proximal hub 304 with the filaments 302 forming loops 314 when expanded (see FIG. 54).

The device 300 may be coupled to a source of energy, such as a source of RF energy, which is delivered to heat the device 300 to adhere the device 300 to the aneurysm and/or shrink the aneurysm. The device may also be used with other methods of closing an aneurysm such as with a sealant or with conventional coils and the like. The device 300 prevents such embolic material from migrating out of the aneurysm.

Referring to FIGS. 57-61, yet another device 316 for treating an aneurysm is shown. The device 316 has a manipulator 318 which may simply push the device 316 through a lumen 320 in a catheter 322 or may be releasably attached in any suitable manner. The device 316 has a plurality of filaments 324 each having a proximal end 326 and a distal end 328. The proximal ends 326 are coupled together at a hub 330.

Figure 58:
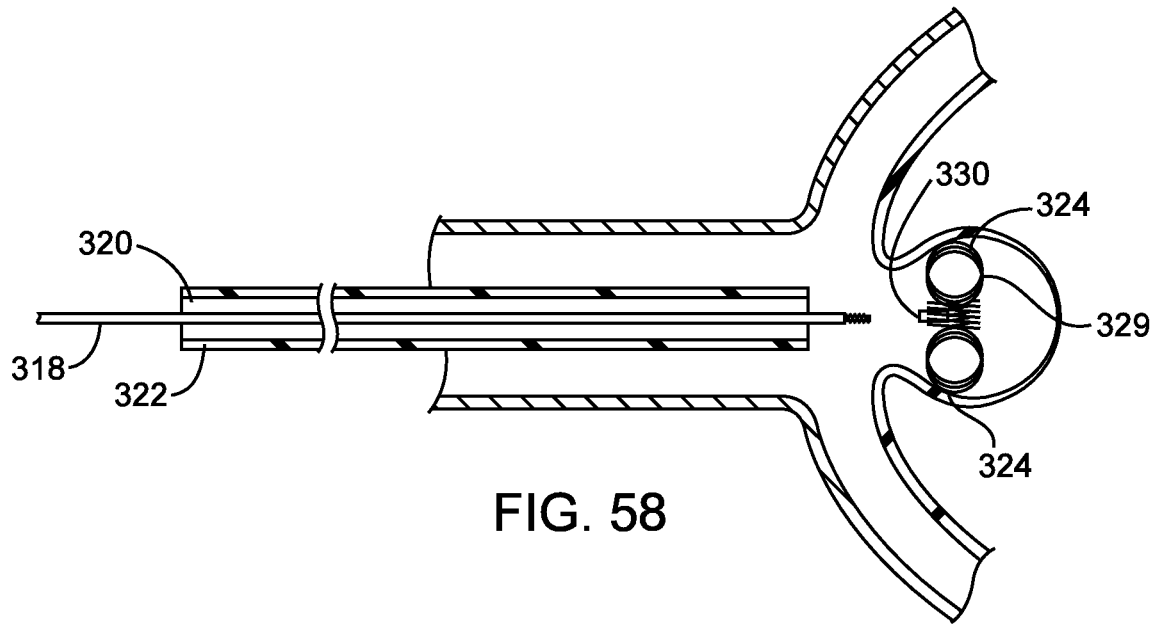
FIG. 58 shows the device of FIG. 57 deployed within an aneurysm.
Figure 59:
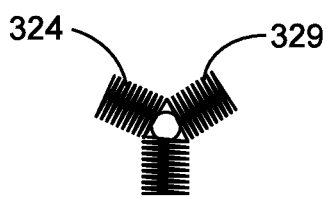
FIG. 59 shows a plan view of the device of FIGS. 57 and 58.
Figure 60:
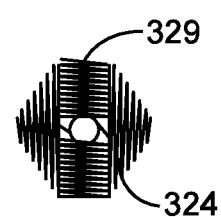
FIG. 60 shows an alternative to the device of FIGS. 57-59.
Figure 61:
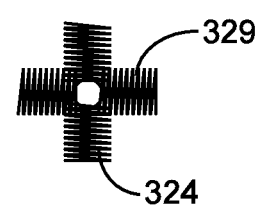
FIG. 61 shows another alternative to the device of FIGS. 57-59.

The filaments 324 are collapsed into a relatively straightened configuration when positioned in the catheter 322. When the filaments 326 are deployed out of the catheter 322, the filaments 324 expand to occupy space in the aneurysm. The filaments 324 may expand into any suitable shape and preferably expand to form a number of coils 328. The coils 328 may be oriented in any manner and are preferably oriented with a central axis 330 of at least three coils 328 lying in a common plane 330. The device 316 may have 2-6 coils 328 and FIG. 59 shows three coils and FIGS. 60 and 61 show two different four coil 328 configurations. The device 316 is deployed in substantially the same manner as the device described above. The catheter 322 is advanced to the aneurysm and the manipulator 318 moves the device 316 out of the catheter and into the aneurysm as shown in FIG. 58.

Figure 64:
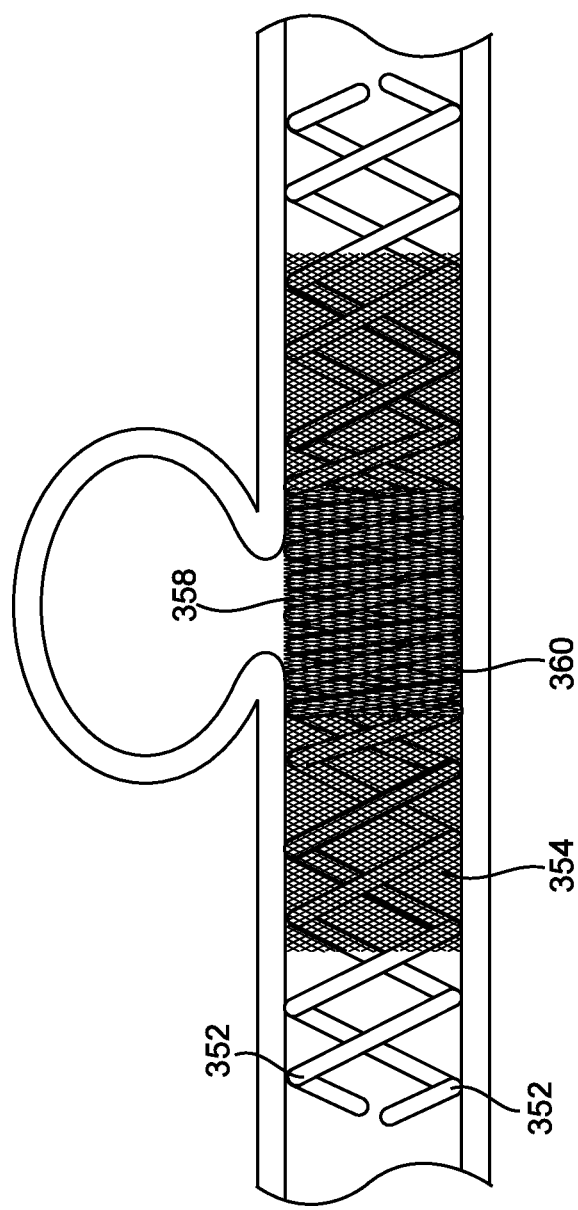
FIG. 64 shows the device used in another malformation.

Referring to FIGS. 62-64, another device 350 for treating a vascular malformation, such as an aneurysm, is shown. In a specific use of the present invention, the device 350 is used for treating cerebral aneurysms although the device 350 may be used at any other suitable vascular location. The device 350 has one or more main coils 352 and one or more secondary coils 354. FIGS. 62-64 show two interwoven helical-shaped main coils 352. The main coils 352 provide structural support and are naturally biased toward the expanded position when released. The secondary coils 354 are held by the main coil 352 and do not add significant structural support for the device and are used primarily to fill spaces in the main coil 352. The device 350 isolates the malformation from the parental vessel thereby reducing blood flow to enhance thrombosis. The device 350 also may be used to prevent migration of natural and implanted embolic materials. The main coil 350 may be formed of any suitable material. For example, the main coil 350 may be made of platinum or another radioopaque material. Other suitable materials include nitinol, steel, and aluminum. The secondary windings 354 may be suture, thread, ePTFE, dacron, polyurethane, a hydrogel, platinum, steel and aluminum. Furthermore, the main coils 352 and/or secondary windings 354 may be coated or otherwise treated to provide radioactivity or drug delivery or a drug coating.

The device 350 may have a more dense mesh 358 along a central portion 360 than at the ends of the device 350. The central portion 360 helps to isolate the aneurysm or other malformation. In FIGS. 62-64, two main coils 352 are wound in opposite directions and are interwoven. The secondary windings 354 have an increased density along the central portion 360 either by providing additional secondary windings 360 or by simply increasing the winding density of the secondary coils 354 or main coils 352.

Figure 69:
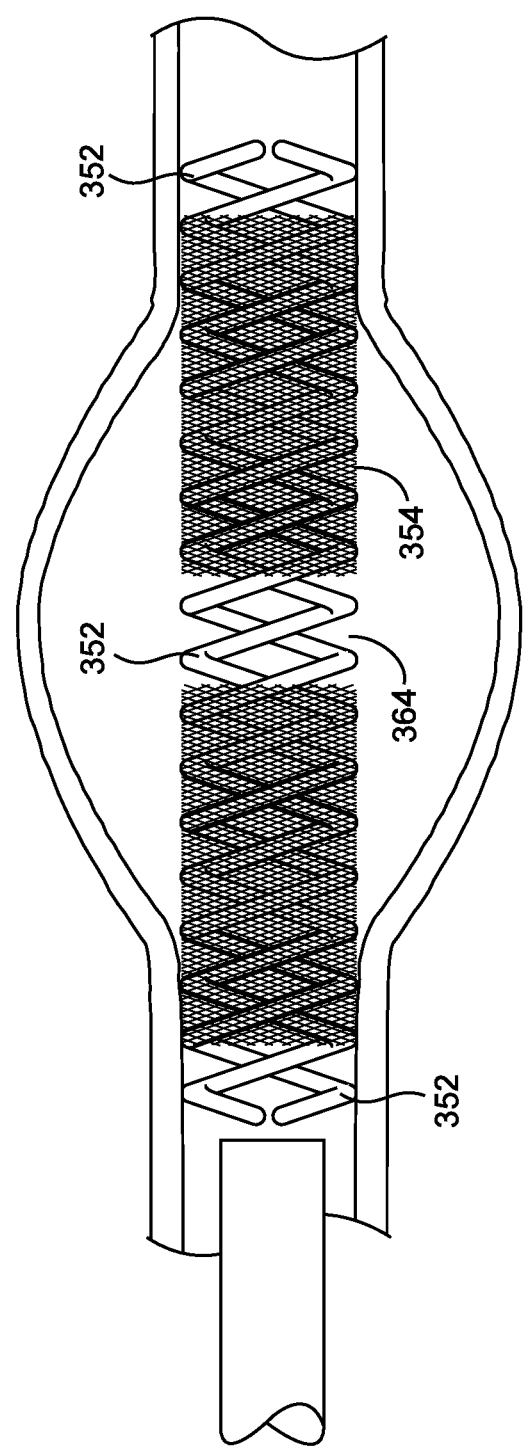
FIG. 69 shows another device for treating a vascular malformation, which has a circumferential opening.
Figure 72:
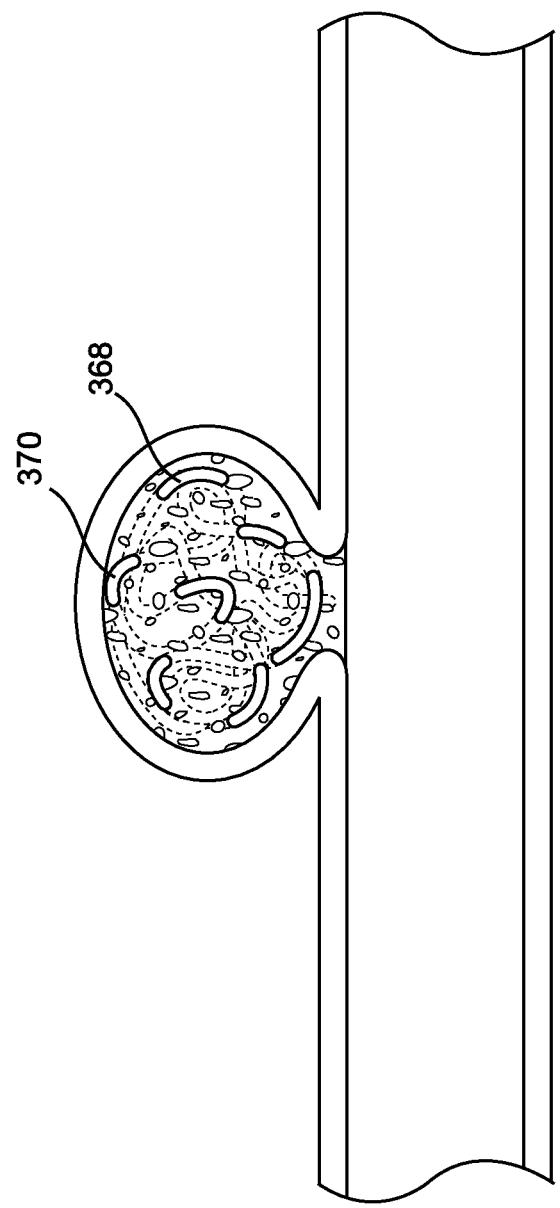
FIG. 72 shows a thrombus formed in the aneurysm after removal of the device of FIGS. 70 and 71.

Referring to FIGS. 65-66, still another device 362 for treating an aneurysm is shown wherein the same or similar reference numbers refer to the same or similar device. The device 362 has a central opening 364 through which embolic materials may be delivered. The opening 364 may simply be formed by a cut-out section 366 as shown in FIGS. 65 and 66. Alternatively, the opening 364 may be provided simply by larger spacings between the main coil 352 or secondary windings 354 as shown in FIGS. 67 and 68. In still another example, the opening 364 may be formed by omitted elements in the main coil 352 or secondary windings 354 as shown in FIG. 69. Embolic elements 368, such as embolic coils, gels, glue, or hydrogels may be delivered through the opening 364. In one aspect, the device 362 is used to deliver a hydrogel 370 which is delivered as in elongate section or filament 371 such as those described in U.S. Prov. Appl. Ser. No. 60/288,458 entitled Hydrogel Filament Vaso-Occlusive Device, U.S. Prov. Appl. Ser. No. 60/288,467 entitled Coated Combination Vaso-Occlusive Device, U.S. Prov. Appl. Ser. No. 60/288,459 entitled Bioactive Polymer Vaso-Occlusive Device, U.S. Prov. Appl. Ser. No. 60/288,494 entitled Hydrogel Vaso-Occlusive Device, and U.S. Prov. Appl. Ser. No. 60/330,619 entitled Device for Vaso-Occlusion and Interventional Therapy which are incorporated here by reference. Devices, systems and methods for delivering the elongate hydrogel 370 are described in U.S. patent application Ser. No. 10/106,483, filed on Mar. 25, 2002, entitled "Containers and Methods for Delivering Vaso-occluding Filaments and Particles" by Dieck et al.

Referring to FIGS. 70-74, still another vascular element 372 is shown for treating an aneurysm. The vascular element 372 has a single coil 374 although other structures may be used without departing from the scope of the invention. The embolic element 368 is delivered to the aneurysm and the vascular element 372 helps to hold the embolic element 368 within the aneurysm. After the embolic element 368 has been delivered and after a length of time to permit thrombus formation in the aneurysm, the vascular element 372 may be removed. The vascular element 372 may either remain attached to an insertion element 374 for removal or a separate retrieval device (not shown) may be used to remove the vascular element 372.

Referring to FIG. 75-78, still another device 378 is shown for treating a malformation such as an aneurysm. A first vascular element 380, such as a first coil 382, is delivered to partially cover the aneurysm. An embolic element 368 may then be delivered through the first element 380. For example, the embolic element 368 may be a hydrogel or embolic coils delivered through a lumen 384 extending through the delivery catheter 386. After delivery of the embolic element 368, a second element 388, such as a second coil 390, is deployed to fill voids or interstitial spaces 392 in the first element 380. When using the first and second coils 382, 390, the second coil 390 preferably extends side-by-side with the first coil 382. A distal end 394 of the second coil 390 may be intertwined with a proximal end 396 of the first coil 382 so that the first and second coils 382, 390 are already engaged with one another. The second coil 390 may then be rotated into engagement with the first coil 382 so that the second coil 390 tracks over the first coil 382. The first and second elements 380, 388 preferably do not overlap although overlapping structures may be used without departing from various aspects of the invention While the above is a description of the preferred embodiments of the invention, various alternatives, modifications, and equivalents may be used. For example, the expandable device may take any other shape and the sealant may be any other suitable sealant. Furthermore, the dimensions and characteristics of any of the expandable members may be incorporated into any of the other expandable devices described herein without departing from the scope of the invention. In addition, the expandable devices are preferably used when shrinking the aneurysm but the expandable devices may have various features which may be useful when simply filling the aneurysm in the conventional manner. Finally, any of the devices described above may also incorporated delivery of energy, such as RF energy, to the device as described in some of the embodiments and incorporation of such energy delivering features are incorporated into each of the devices described herein for all purposes.

What is claimed is:

1. A method of filling an aneurysm, comprising the steps of:

advancing a device through a patient's vascular system to an aneurysm, the device being a closed mesh structure formed of a plurality of flexible filaments, the device having a proximal collar and a distal collar with the flexible filaments extending therebetween, the closed mesh structure being movable from a collapsed configuration to an expanded configuration, the closed mesh structure forming a tubular structure in the collapsed configuration, the closed mesh structure further having a first expandable section and a second expandable section, the first expandable section being coupled to the proximal collar and the second expandable section being coupled to the distal collar, the first expandable section being less permeable to fluid than the second expandable section; and positioning the device in the expanded position within the aneurysm, the proximal collar being positioned adjacent a neck of the aneurysm and the distal collar being positioned adjacent a dome of the aneurysm, the positioning step also being carried out with the first expandable section being positioned adjacent the neck of the aneurysm and the second expandable section being positioned adjacent the dome of the aneurysm.

2. The method of claim 1, wherein:

the positioning step is carried out with the device not extending into a parental vessel of the aneurysm.

3. The method of claim 1, wherein:

the advancing step is carried out with the proximal collar being coupled to a wire, the wire being detachable from the proximal collar.

\* \* \* \* \*